United States Patent
Hayashita et al.

(10) Patent No.: US 9,745,911 B2
(45) Date of Patent: Aug. 29, 2017

(54) CONTROL SYSTEM OF INTERNAL COMBUSTION ENGINE

(71) Applicants: Go Hayashita, Ebina (JP); Keiichiro Aoki, Shizuoka (JP)

(72) Inventors: Go Hayashita, Ebina (JP); Keiichiro Aoki, Shizuoka (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 71 days.

(21) Appl. No.: 14/763,555

(22) PCT Filed: Jan. 29, 2013

(86) PCT No.: PCT/JP2013/051918
§ 371 (c)(1),
(2) Date: Jul. 27, 2015

(87) PCT Pub. No.: WO2014/118896
PCT Pub. Date: Aug. 7, 2014

(65) Prior Publication Data
US 2016/0017828 A1    Jan. 21, 2016

(51) Int. Cl.
*F02D 41/14* (2006.01)
*G01N 27/406* (2006.01)
*F02D 41/00* (2006.01)

(52) U.S. Cl.
CPC ..... *F02D 41/1454* (2013.01); *F02D 41/1441* (2013.01); *G01N 27/4065* (2013.01); *F02D 41/1401* (2013.01); *F02D 41/1456* (2013.01)

(58) Field of Classification Search
CPC ............. F02D 41/1454; F02D 41/1441; F02D 41/1401; F02D 41/1456
(Continued)

(56) References Cited

U.S. PATENT DOCUMENTS

| 4,450,065 A | 5/1984 | Yamada et al. |
| 4,839,018 A | 6/1989 | Yamada et al. |
| 5,686,654 A * | 11/1997 | Friese .................. G01N 27/419 60/276 |
| 5,758,490 A | 6/1998 | Maki et al. |
| 6,099,717 A | 8/2000 | Yamada et al. |
| 2002/0050455 A1 | 5/2002 | Kurokawa et al. |
| 2003/0183520 A1 | 10/2003 | Mabuchi et al. |
| 2004/0149008 A1 | 8/2004 | Allmendinger |
| 2005/0061667 A1 | 3/2005 | Suzuki |
| 2008/0196702 A1 * | 8/2008 | Fukagai .............. F02D 41/1456 123/688 |

(Continued)

FOREIGN PATENT DOCUMENTS

EP  1202048 A2  5/2002
JP  S58-153155 A  9/1983
(Continued)

*Primary Examiner* — Mahmoud Gimie
(74) *Attorney, Agent, or Firm* — Andrews Kurth Kenyon LLP

(57) ABSTRACT

This control device for an internal combustion engine is equipped with: an air/fuel ratio sensor provided to the exhaust passage of an internal combustion engine; and an engine control device that controls the internal combustion engine according to the output of the air/fuel ratio sensor. The air/fuel ratio sensor is equipped with: a gas chamber to be measured, into which exhaust gas flows; a pump cell that pumps oxygen into or out of the gas chamber to be measured according to the pump current; and a reference cell of which the reference cell output current detected varies according to the air/fuel ratio inside the gas chamber to be measured. The reference cell is equipped with: a first electrode that is exposed to the exhaust gas in the gas chamber to be measured; a second electrode exposed to a reference atmosphere; and a solid electrolyte layer arranged between the electrodes. The air/fuel ratio sensor is equipped with: a reference cell voltage applying device that applies a sensor applied voltage between the electrodes; and a reference cell output current detection device that detects, as the reference cell output current, the current flowing between the electrodes.

10 Claims, 16 Drawing Sheets

(58) Field of Classification Search
USPC .............. 123/672, 703; 701/109; 60/276
See application file for complete search history.

(56) References Cited

U.S. PATENT DOCUMENTS

| | | |
|---|---|---|
| 2009/0090339 A1 | 4/2009 | Kerns et al. |
| 2010/0122568 A1 | 5/2010 | Inoue et al. |
| 2015/0369156 A1* | 12/2015 | Hayashita ............ F02D 41/1473 60/285 |

FOREIGN PATENT DOCUMENTS

| | | |
|---|---|---|
| JP | H04-204370 A | 7/1992 |
| JP | 08-232723 A | 9/1996 |
| JP | 2000-356618 A | 12/2000 |
| JP | 2001-234787 A | 8/2001 |
| JP | 2002-202285 A | 7/2002 |
| JP | 2002-357589 A | 12/2002 |
| JP | 2003-329637 A | 11/2003 |
| JP | 2004-258043 A | 9/2004 |
| JP | 2005-351096 A | 12/2005 |
| JP | 3849678 B2 | 11/2006 |
| JP | 2009-162139 A | 7/2009 |
| JP | 2010-121951 A | 6/2010 |
| JP | 2011-069337 A | 4/2011 |
| JP | 2011-069338 A | 4/2011 |

\* cited by examiner (A)

(B)

(A)

(B)

(C)

(A)

(B)

(C)

CONTROL SYSTEM OF INTERNAL COMBUSTION ENGINE

CROSS-REFERENCE TO RELATED APPLICATION

This is a national phase application based on the PCT International Patent Application No. PCT/JP2013/051918 filed Jan. 29, 2013, the entire contents of which are incorporated herein by reference.

TECHNICAL FIELD

The present invention relates to a control system of an internal combustion engine which controls the internal combustion engine in accordance with the output of an air-fuel ratio sensor.

BACKGROUND ART

In the past, a control system of an internal combustion engine which is provided with an air-fuel ratio sensor in an exhaust passage of the internal combustion engine and controls the amount of fuel fed to the internal combustion engine based on the output of this air-fuel ratio sensor, has been widely known. Further, the air-fuel ratio sensor which is used in such a control system has also been widely known (for example, see PLTs 1 to 6).

Such air-fuel ratio sensors may be roughly divided into single-cell types of air-fuel ratio sensors (for example, PLTs 2 and 4) and double-cell types of air-fuel ratio sensors (for example, PLTs 1, 3, and 5). In a single-cell type of air-fuel ratio sensor, only a single cell comprised of a solid electrolyte layer which can pass oxygen ions and two electrodes which are provided on both side surfaces of the layer, is provided. One of the electrodes thereof is exposed to the atmosphere, while the other electrode is exposed to the exhaust gas through a diffusion regulating layer. In the thus configured single-cell type of air-fuel ratio sensor, voltage is applied across two electrodes which are arranged on the both side surfaces of the solid electrolyte layer. Along with this, between the two side surfaces of the solid electrolyte layer, movement of oxygen ions occurs in accordance with the ratio of concentration of oxygen between these side surfaces. By detecting the current generated by this movement of oxygen ions, the air-fuel ratio of the exhaust gas (below, also referred to as the "exhaust air-fuel ratio") is detected (for example, PLT 2)

On the other hand, in a double-cell type of air-fuel ratio sensor, two cells, each comprised of a solid electrolyte layer which can pass oxygen ions and two electrodes which are provided on both side surfaces of the layer, are provided. One cell (reference cell) among these is configured so that the detected voltage (electromotive force) changes in accordance with a concentration of oxygen in exhaust gas in a measured gas chamber. Further, the other cell (pump cell) pumps oxygen in and pumps it out with respect to the exhaust gas in the measured gas chamber, in accordance with a pump current. In particular, the pump current of the pump cell is set so as to pump in oxygen and pump it out so as to make the detected voltage which is detected at the reference cell conform to a target voltage value. By detecting this pump current, the exhaust air-fuel ratio is detected.

CITATION LIST

Patent Literature

PLT 1: Japanese Patent Publication No. 2002-357589A
PLT 2: Japanese Patent Publication No. 2005-351096A
PLT 3: Japanese Patent Publication No. 2004-258043A
PLT 4: Japanese Patent Publication No. 2000-536618A
PLT 5: Japanese Patent Publication No. H4-204370A
PLT 6: Japanese Patent Publication No. S58-153155A

SUMMARY OF INVENTION

Technical Problem

In this regard, a single-cell type of air-fuel ratio sensor and a double-cell type of air-fuel ratio sensor will be compared. In each air-fuel ratio sensor, the solid electrolyte layer is directly or indirectly exposed to exhaust gas, and therefore aging causes the internal resistance of the solid electrolyte layer to change. Further, the internal resistance of the solid electrolyte layer fluctuates due to the temperature, and therefore when the temperature of the solid electrolyte layer is not being accurately controlled, the internal resistance of the solid electrolyte layer also changes.

In a single-cell type of air-fuel ratio sensor, even if the exhaust air-fuel ratio is the same, if the internal resistance of the solid electrolyte layer changes, its output current will change. Therefore, if not performing temperature control with a high precision, the precision of detection of the air-fuel ratio will fall. On top of that, even if controlling the temperature with a high precision, aging will cause the precision of detection of the air-fuel ratio to fall. As opposed to this, in a pump cell of a double-cell type of air-fuel ratio sensor, the relationship between the pump current and the flow rate of oxygen pumped into or pumped out from the inside of the measured gas chamber will remain constant, even if the internal resistance changes. Therefore, in a pump cell, there is no effect on output even if the internal resistance changes. Further, in a reference cell, only the electromotive force, which does not change due to the internal resistance, is detected, and therefore there is no effect on output even if the internal resistance changes. Therefore, in a double-cell type of air-fuel ratio sensor, compared with a single-cell type of air-fuel ratio sensor, even if aging or poor control of the temperature causes the internal resistance to change, the air-fuel ratio can be detected with a high precision.

FIG. 2 (is a view which shows the output characteristics in a double-cell type of air-fuel ratio sensor and a single-cell type of air-fuel ratio sensor. FIG. 2(B) shows the relationship between a voltage Vr which is applied across electrodes which form a cell, and an output current Ir, in a single-cell type of air-fuel ratio sensor. As will be understood from FIG. 2(B), the voltage region, in which a limit current (output current when even if making the applied voltage change, the output current does not change much at all) is generated, changes depending on the exhaust air-fuel ratio. Therefore, if making the applied voltage constant (for example, one-dot chain line in the figure), the range of the detectable air-fuel ratio will be limited. On the other hand, to detect the air-fuel ratio over a broad range, it is necessary to change the applied voltage according to the output current (for example, two-dot chain line in figure). However, such control is complicated and in addition, it is necessary to measure the voltage region where the limit current is generated in advance for each sensor.

On the other hand, FIG. 2(A) shows the relationship between the target voltage value Vt when setting the pump current and the pump current (output current) Ip, in a double-cell type of air-fuel ratio sensor. As will be understood from FIG. 2(A), the voltage region where the limit current is generated is substantially constant regardless of the exhaust air-fuel ratio. Therefore, if making the target voltage value constant, the air-fuel ratio can be detected over a broad range. In this way, according to a double-cell type of air-fuel ratio sensor, the air-fuel ratio can be detected over a broader range compared with a single-cell type of air-fuel ratio sensor.

On the other hand, in a double-cell type of air-fuel ratio sensor, a reference cell is used in which an electromotive force is generated depending on the concentration ratio of oxygen in the exhaust gas in the measured gas chamber and the concentration of oxygen in the atmosphere. In such a reference cell, the relationship between the air-fuel ratio and the output voltage changes when the exhaust air-fuel ratio changes from rich to lean and when it changes from lean to rich.

FIG. 3 is a view which shows the relationship between the air-fuel ratio and detection voltage (electromotive force) in a reference cell. As shown in FIG. 3 by the solid line "rich→lean", when making the air-fuel ratio change from one richer than the stoichiometric air-fuel ratio (below, also called "rich air-fuel ratio") to one leaner than the stoichiometric air-fuel ratio (below, also called "lean air-fuel ratio"), even when the actual air-fuel ratio becomes the lean air-fuel ratio, for a while the electromotive force maintains a high state. On the other hand, as shown in FIG. 3 by the solid line "lean→rich", when making the air-fuel ratio change from the lean air-fuel ratio to the rich air-fuel ratio, even when the actual air-fuel ratio becomes the rich air-fuel ratio, for a while the electromotive force maintains a low state. In this way, a reference cell has hysteresis in accordance with the direction of change of the air-fuel ratio. A reference cell has hysteresis in such a way because the reactivity of unburned gas or oxygen on the electrodes is low, and because in actuality, the electromotive force is delayed in tracking the air-fuel ratio.

As a result of the reference cell having hysteresis in this way, as shown in FIG. 4, the output current (pump current) of the double-cell type air-fuel ratio sensor for the same air-fuel ratio become different values between when the air-fuel ratio changes in the rich direction (that is, when it changes from the relatively lean state to the rich state) and when the air-fuel ratio changes in the lean direction (that is, when it changes from the relatively rich state to the lean state).

Further, the solid lines in FIG. 3 show the case where the ingredients contained in the exhaust gas are CO and NO, while the broken lines show the case where the ingredients contained in the exhaust gas are CO and $O_2$. As will be understood from FIG. 3, the solid lines and broken lines deviate from each other. In the reference cell, it can be said that the relationship between the air-fuel ratio and electromotive force changes depending on the ingredients in the exhaust gas. The relationship between the air-fuel ratio and electromotive force changes depending on the composition of ingredients contained in the exhaust gas (CO, HC, $NO_X$, $O_2$, etc.) in this way, because the reactivity on the electrodes of the reference cell differs for each ingredient in the exhaust gas and, as a result, the response differs for each ingredient in the exhaust gas. As a result, in a double-cell type of air-fuel ratio sensor, even if the exhaust air-fuel ratio is the same, sometimes the output current (pump current) changes depending on the composition of the ingredients in the exhaust gas.

Therefore, in consideration of the above problems, an object of the present invention is to provide an air-fuel ratio sensor which overcomes the defects of both the conventional single-cell type air-fuel ratio sensors and double-cell type air-fuel ratio sensors.

Solution to Problem

To solve the above problem, in a first aspect of the invention, there is provided a control system of an internal combustion engine, comprising: an air-fuel ratio sensor which is provided in an exhaust passage of the internal combustion engine; and an engine control device which controls the internal combustion engine in accordance with a sensor output current of the air-fuel ratio sensor, wherein the air-fuel ratio sensor comprises: a measured gas chamber into which exhaust gas which is to be detected for air-fuel ratio flows; a pump cell which pumps in oxygen to and pumps out oxygen from the exhaust gas in the measured gas chamber in accordance with a pump current; and a reference cell with a detected reference cell output current which changes in accordance with the air-fuel ratio in the measured gas chamber, the reference cell comprises: a first electrode which is exposed to exhaust gas inside the measured gas chamber; a second electrode which is exposed to a reference atmosphere; and a solid electrolyte layer which is arranged between the first electrode and the second electrode, the air-fuel ratio sensor comprises: a reference cell voltage application device which applies a sensor applied voltage between the first electrode and second electrode of the reference cell; a reference cell output current detection device which detects a current which flows between the first electrode and second electrode of the reference cell as the reference cell output current; a pump current control device which controls a pump current, which flows at a pump cell, so that the reference cell output current which is detected by the reference cell output current detection device becomes a target current value; and a pump current detection device which detects the pump current as the sensor output current, and the target current at the pump current control device is zero.

In a second aspect of the invention, there is provided the first aspect of the invention, wherein the air-fuel ratio sensor further comprises a diffusion regulating layer and the diffusion regulating layer is arranged so that a first electrode of the reference cell is exposed to exhaust gas inside the measured gas chamber through the diffusion regulating layer.

In a third aspect of the invention, there is provided the first or second aspect of the invention, wherein the air-fuel ratio sensor further comprises an atmospheric air chamber in which the second electrode is exposed, the reference atmosphere is the atmospheric air, and that atmospheric air chamber is configured so that atmospheric air can be introduced.

In a fourth aspect of the invention, there is provided any one of the first to third aspects of the invention, wherein the pump cell comprises: a third electrode which is exposed to exhaust gas in the measured gas chamber; a fourth electrode which is exposed to exhaust gas around the air-fuel ratio sensor; and a solid electrolyte layer which is arranged between the third electrode and the fourth electrode, and the pump current control device controls the pump current which flows across the third electrode and fourth electrode through a solid electrolyte layer of the pump cell.

In a fifth aspect of the invention, there is provided any one of the first to fourth aspects of the invention, wherein the reference cell is configured so that the sensor applied voltage, by which the reference cell output current becomes zero, changes in accordance with the air-fuel ratio of exhaust gas in the measured gas chamber and if increasing the sensor applied voltage at the reference cell when the exhaust gas is the stoichiometric air-fuel ratio, the reference cell output current increases along with that, and the sensor applied voltage at the reference cell is fixed to a constant voltage, and the constant voltage is a voltage by which the reference cell output current becomes zero when the air-fuel ratio of the exhaust gas in the measured gas chamber is the stoichiometric air-fuel ratio.

In a sixth aspect of the invention, there is provided the fifth aspect of the invention, wherein the internal combustion engine further comprises an exhaust purification catalyst which is provided at an upstream side, in the direction of flow of exhaust, from the air-fuel ratio sensor in the exhaust passage, and which can store oxygen, and the engine control device comprises: an oxygen storage amount increasing means for making a target air-fuel ratio of exhaust gas which flows into the exhaust purification catalyst, continuously or intermittently leaner than the stoichiometric air-fuel ratio, when the sensor output current of the air-fuel ratio sensor has become a rich judged reference value corresponding to a rich judged air-fuel ratio lower than the stoichiometric air-fuel ratio, until the oxygen storage amount of the exhaust purification catalyst becomes a predetermined storage amount smaller than the maximum oxygen storage amount; and an oxygen storage amount decreasing means for making the target air-fuel ratio continuously or intermittently richer than the stoichiometric air-fuel ratio, when the oxygen storage amount of the exhaust purification catalyst has become the predetermined storage amount or more, so that the oxygen storage amount decreases toward zero without reaching the maximum oxygen storage amount.

In a seventh aspect of the invention, there is provided any one of the first to fourth aspects of the invention, wherein the reference cell is configured so that the sensor applied voltage, by which the reference cell output current becomes zero, changes in accordance with the air-fuel ratio of exhaust gas in the measured gas chamber and if increasing the sensor applied voltage at the reference cell when the exhaust gas is the stoichiometric air-fuel ratio, the reference cell output current increases along with that, and the sensor applied voltage at the reference cell is fixed to a constant voltage, and the constant voltage is a voltage different from the voltage by which the reference cell output current becomes zero when the air-fuel ratio of the exhaust gas in the measured gas chamber is the stoichiometric air-fuel ratio and a voltage by which the reference cell output current becomes zero when the air-fuel ratio of the exhaust gas is an air-fuel ratio which is different from the stoichiometric air-fuel ratio.

In an eighth aspect of the invention, there is provided the seventh aspect of the invention, wherein the reference cell is configured so as to have a limit current region of a voltage region where the reference cell output current becomes a limit current for each exhaust air-fuel ratio, and the constant voltage is a voltage inside the limit current region when the exhaust air-fuel ratio is the stoichiometric air-fuel ratio.

In a ninth aspect of the invention, there is provided the seventh or eighth aspect of the invention, wherein the internal combustion engine comprises an exhaust purification catalyst which is provided at an upstream side, in the direction of flow of exhaust, from the air-fuel ratio sensor in the exhaust passage, and which can store oxygen, and the constant voltage is a voltage whereby the reference cell output current becomes zero when the exhaust air-fuel ratio is a predetermined air-fuel ratio which is richer than the stoichiometric air-fuel ratio.

In a tenth aspect of the invention, there is provided the ninth aspect of the invention, wherein the engine control device comprises: an oxygen storage amount increasing means for making a target air-fuel ratio of exhaust gas which flows into the exhaust purification catalyst continuously or intermittently leaner than the stoichiometric air-fuel ratio, when the sensor output current of the air-fuel ratio sensor has become zero or less, until the oxygen storage amount of the exhaust purification catalyst becomes a predetermined storage amount smaller than the maximum oxygen storage amount; and an oxygen storage amount decreasing means for making the target air-fuel ratio continuously or intermittently richer than the stoichiometric air-fuel ratio, when the oxygen storage amount of the exhaust purification catalyst has become the predetermined storage amount or more, so that the oxygen storage amount decreases toward zero without reaching the maximum oxygen storage amount.

Advantageous Effects of Invention

According to the present invention, an air-fuel ratio sensor which overcomes the defects of both the conventional single-cell type air-fuel ratio sensors and double-cell type air-fuel ratio sensors can be provided.

DESCRIPTION OF EMBODIMENTS

Figure 1:
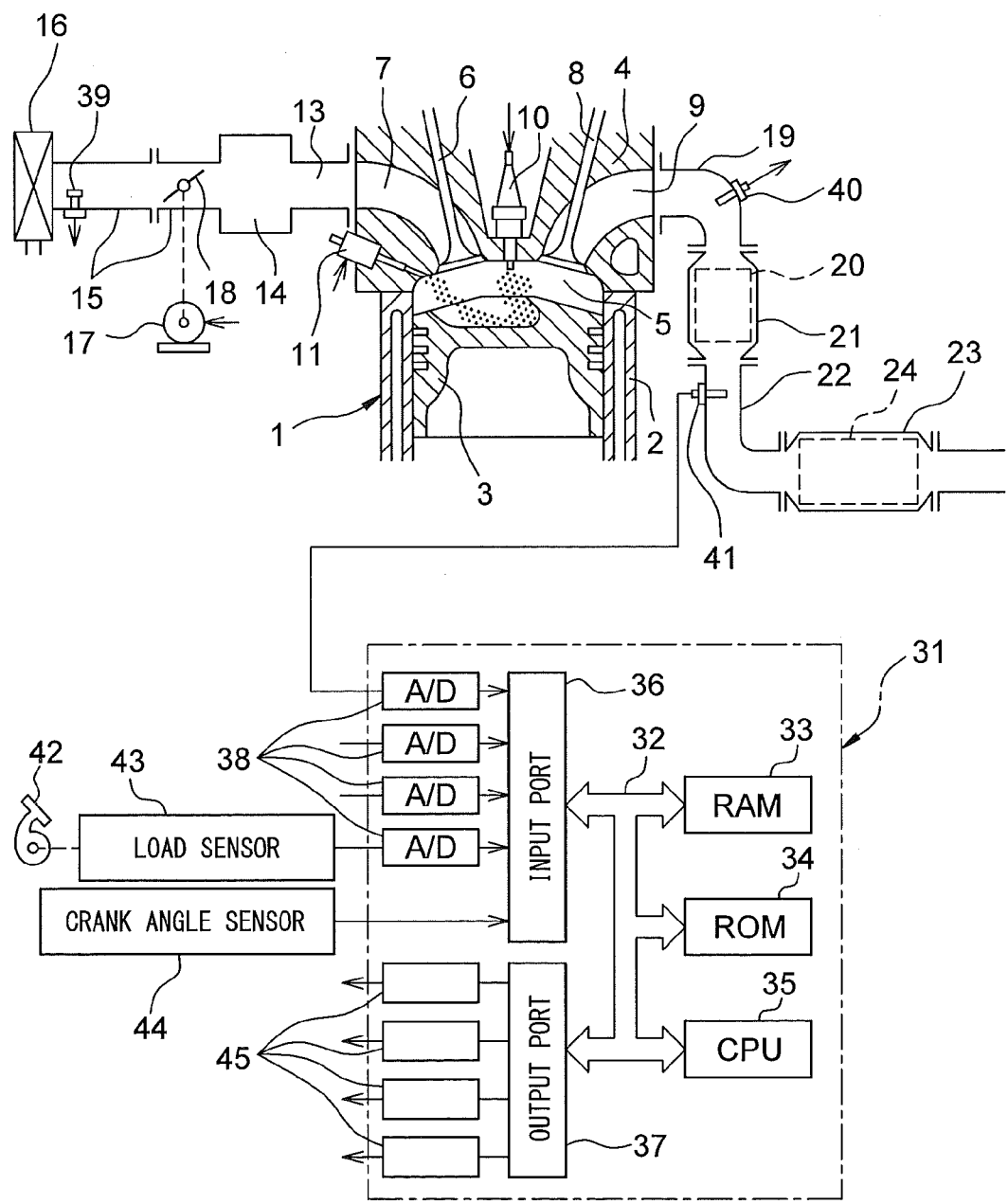
FIG. 1 is a view which schematically shows an internal combustion engine in which a control system of the present invention is used.
Figure 2:
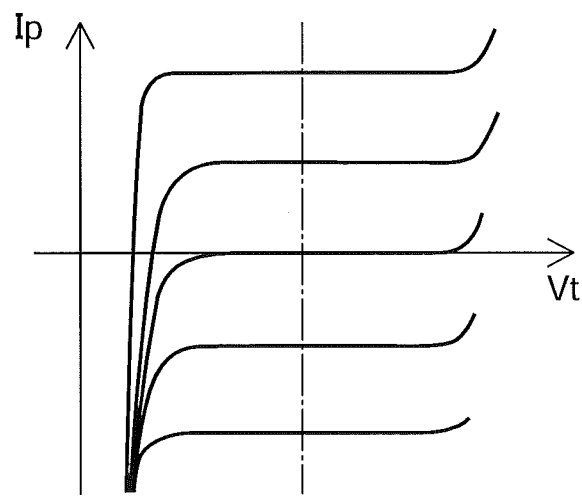
FIG. 2 is a view which shows output characteristics in a double-cell type of air-fuel ratio sensor and a single-cell type of air-fuel ratio sensor.
Figure 2:
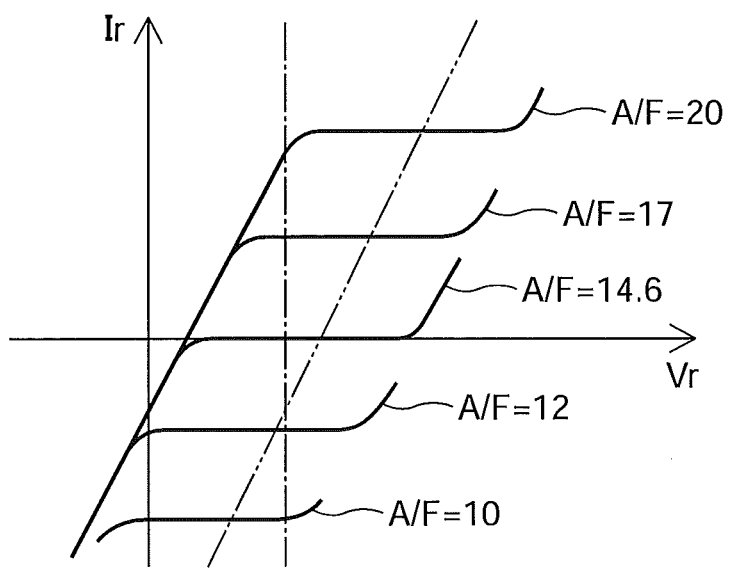
Figure 3:
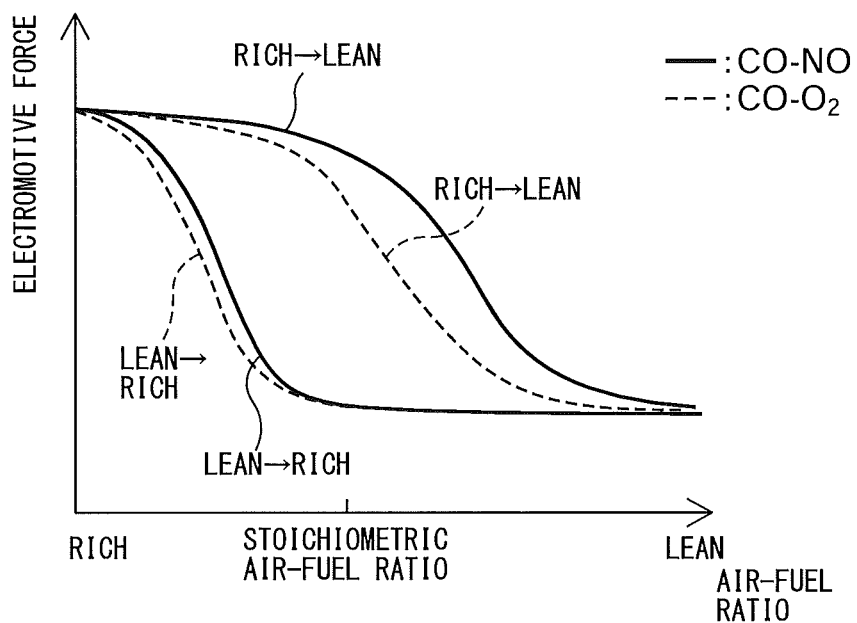
FIG. 3 is a view which shows the relationship between the air-fuel ratio and detected voltage (electromotive force) in a conventional reference cell.
Figure 4:
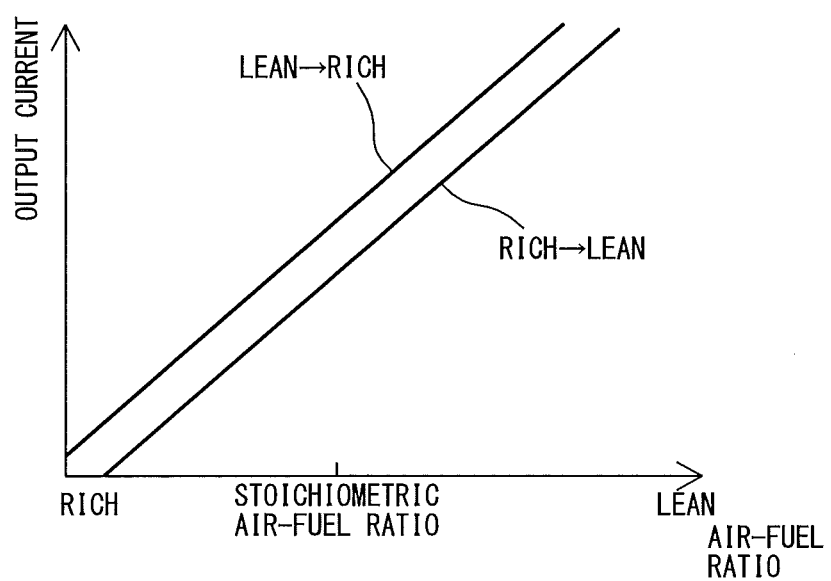
FIG. 4 is a view which shows the relationship between the air-fuel ratio and sensor output current in a conventional double-cell type of air-fuel ratio sensor.

Below, referring to the drawings, a control device of an internal combustion engine of the present invention will be explained in detail. Note that, in the following explanation, similar component elements are assigned the same reference numerals. FIG. 1 is a view which schematically shows an internal combustion engine in which a control device according to a first embodiment of the present invention is used.

<Explanation of Internal Combustion Engine as a Whole>

Referring to FIG. 1, 1 indicates an engine body, 2 a cylinder block, 3 a piston which reciprocates inside the cylinder block 2, 4 a cylinder head which is fastened to the cylinder block 2, 5 a combustion chamber which is formed between the piston 3 and the cylinder head 4, 6 an intake valve, 7 an intake port, 8 an exhaust valve, and 9 an exhaust port. The intake valve 6 opens and closes the intake port 7, while the exhaust valve 8 opens and closes the exhaust port 9.

As shown in FIG. 1, a spark plug 10 is arranged at a center part of an inside wall surface of the cylinder head 4, while a fuel injector 11 is arranged at a side part of the inner wall surface of the cylinder head 4. The spark plug 10 is configured to generate a spark in accordance with an ignition signal. Further, the fuel injector 11 injects a predetermined amount of fuel into the combustion chamber 5 in accordance with an injection signal. Note that, the fuel injector 11 may also be arranged so as to inject fuel into the intake port 7. Further, in the present embodiment, as the fuel, gasoline with a stoichiometric air-fuel ratio of 14.6 at an exhaust purification catalyst is used. However, the internal combustion engine of the present invention may also use another fuel.

The intake port 7 of each cylinder is connected to a surge tank 14 through a corresponding intake branch pipe 13, while the surge tank 14 is connected to an air cleaner 16 through an intake pipe 15. The intake port 7, intake branch pipe 13, surge tank 14, and intake pipe 15 form an intake passage. Further, inside the intake pipe 15, a throttle valve 18 which is driven by a throttle valve drive actuator 17 is arranged. The throttle valve 18 can be operated by the throttle valve drive actuator 17 to thereby change the aperture area of the intake passage.

On the other hand, the exhaust port 9 of each cylinder is connected to an exhaust manifold 19. The exhaust manifold 19 has a plurality of branch pipes which are connected to the exhaust ports 9 and a header at which these branch pipes are collected. The header of the exhaust manifold 19 is connected to an upstream side casing 21 which houses an upstream side exhaust purification catalyst 20. The upstream side casing 21 is connected through an exhaust pipe 22 to a downstream side casing 23 which houses a downstream side exhaust purification catalyst 24. The exhaust port 9, exhaust manifold 19, upstream side casing 21, exhaust pipe 22, and downstream side casing 23 form an exhaust passage.

The electronic control unit (ECU) 31 is comprised of a digital computer which is provided with components which are connected together through a bidirectional bus 32 such as a RAM (random access memory) 33, ROM (read only memory) 34, CPU (microprocessor) 35, input port 36, and output port 37. In the intake pipe 15, an air flow meter 39 is arranged for detecting the flow rate of air flowing through the intake pipe 15. The output of this air flow meter 39 is input through a corresponding AD converter 38 to the input port 36. Further, at the header of the exhaust manifold 19, an upstream side air-fuel ratio sensor 40 is arranged which detects the air-fuel ratio of the exhaust gas flowing through the inside of the exhaust manifold 19 (that is, the exhaust gas flowing into the upstream side exhaust purification catalyst 20). In addition, in the exhaust pipe 22, a downstream side air-fuel ratio sensor 41 is arranged which detects the air-fuel ratio of the exhaust gas flowing through the inside of the exhaust pipe 22 (that is, the exhaust gas flowing out from the upstream side exhaust purification catalyst 20 and flows into the downstream side exhaust purification catalyst 24). The outputs of these air-fuel ratio sensors 40 and 41 are also input through the corresponding AD converters 38 to the input port 36. Note that, the configurations of these air-fuel ratio sensors 40 and 41 will be explained later.

Further, an accelerator pedal 42 has a load sensor 43 connected to it which generates an output voltage which is proportional to the amount of depression of the accelerator pedal 42. The output voltage of the load sensor 43 is input to the input port 36 through a corresponding AD converter 38. The crank angle sensor 44 generates an output pulse every time, for example, a crankshaft rotates by 15 degrees. This output pulse is input to the input port 36. The CPU 35 calculates the engine speed from the output pulse of this crank angle sensor 44. On the other hand, the output port 37 is connected through corresponding drive circuits 45 to the spark plugs 10, fuel injectors 11, and throttle valve drive actuator 17. Note that the ECU 31 functions as an engine control system for controlling the internal combustion engine based on the outputs of various sensors, etc.

<Configuration of Air-Fuel Ratio Sensor>

Figure 5:
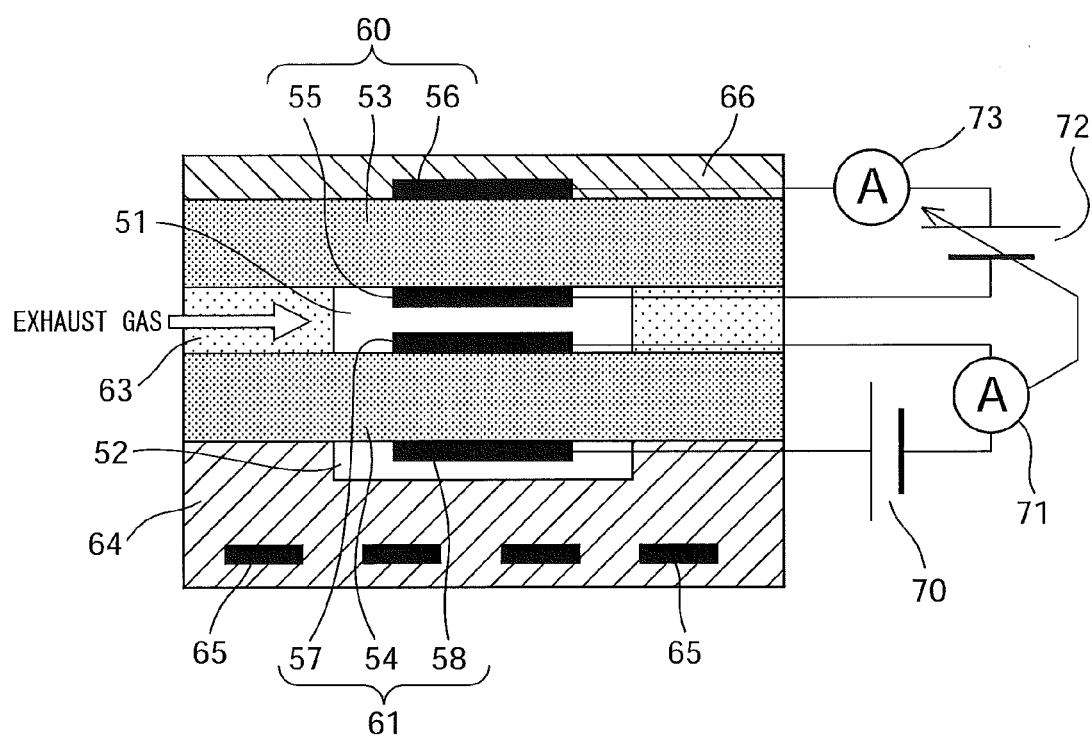
FIG. 5 is a schematic cross-sectional view of an air-fuel ratio sensor.

Next, referring to FIG. 5, the configurations of air-fuel ratio sensors 40 and 41 in the present embodiment will be explained. FIG. 5 is a schematic cross-sectional view of air-fuel ratio sensors 40 and 41. As will be understood from FIG. 5, the air-fuel ratio sensors 40 and 41 in the present embodiment are double-cell type air-fuel ratio sensors each comprised of a solid electrolyte layer and a pair of electrodes forming a double cell.

As shown in FIG. 5, each of the air-fuel ratio sensors 40, 41 comprises a measured gas chamber 51, a reference gas chamber 52, and two solid electrolyte layers 53, 54 which are arranged at the both sides of the measured gas chamber 51. The reference gas chamber 52 is provided at the opposite side of the measured gas chamber 51 across the second solid electrolyte layer 54. On the side surface of the first solid electrolyte layer 53 at the measured gas chamber 51 side, a gas chamber side electrode (third electrode) 55 is arranged, while on the side surface of the first solid electrolyte layer 53 at the exhaust gas side, an exhaust side electrode (fourth electrode) 56 is arranged. These first solid electrolyte layer 53, gas chamber side electrode 55, and exhaust side electrode 56 configure a pump cell 60.

On the other hand, on the side surface of the second solid electrolyte layer 54 at the measured gas chamber 51 side, a gas chamber side electrode (first electrode) 57 is arranged, while on the side surface of the second solid electrolyte layer 54 at the reference gas chamber 52 side, a reference side electrode (second electrode) 58 is arranged. These second solid electrolyte layer 54, gas chamber side electrode 57, and reference side electrode 58 configure a reference cell 61.

Between the two solid electrolyte layers 53 and 54, a diffusion regulating layer 63 is provided so as to surround the gas chamber side electrode 55 of the pump cell 60 and the gas chamber side electrode 57 of the reference cell 61. Therefore, the measured gas chamber 51 is defined by the first solid electrolyte layer 53, the second solid electrolyte layer 54, and the diffusion regulating layer 63. Into the measured gas chamber 51, exhaust gas flows through the diffusion regulating layer 63. Accordingly, the electrodes arranged in the measured gas chamber 51, that is, the gas chamber side electrode 55 of the pump cell 60 and the gas chamber side electrode 57 of the reference cell 61, are exposed through the diffusion regulating layer 63 to the exhaust gas. Note that, the diffusion regulating layer 63 does not necessarily have to be provided so that exhaust gas flowing into the measured gas chamber 51 can pass through the diffusion regulating layer 63. So long as the exhaust gas which reaches the gas chamber side electrode 57 of the reference cell 61 is exhaust gas which passes through the diffusion regulating layer, the diffusion regulating layer may be arranged in any manner.

Further, on the side surface of the second solid electrolyte layer 54 at the reference gas chamber 52 side, a heater part 64 is provided so as to surround the reference gas chamber 52. Therefore, the reference gas chamber 52 is defined by the second solid electrolyte layer 54 and the heater part 64. In this reference gas chamber 52, reference gas is introduced. In the present embodiment, the reference gas chamber 52 is opened to the atmosphere. Accordingly, inside the reference gas chamber 52, atmospheric air is introduced as reference gas.

Further, the heater part 64 is provided with a plurality of heaters 65. These heaters 65 can be used to control the temperature of the air-fuel ratio sensors 40, 41, in particular the temperature of the solid electrolyte layers 53, 54. The heater part 65 has a sufficient heat generating capacity for heating the solid electrolyte layers 53, 54 until activating. In addition, on the side surface of the first solid electrolyte layer 53 at the exhaust gas side, a protective layer 66 is provided. The protective layer 66 is formed from a porous material so that liquid in the exhaust gas, etc., is prevented from directly sticking to the exhaust side electrode 56 while the exhaust gas reaches the exhaust side electrode 56.

The solid electrolyte layers 53, 54 are formed by a sintered body of $ZrO_2$ (zirconia), $HfO_2$, $ThO_2$, $Bi_2O_2$, or other oxygen ion conducting oxide in which CaO, MgO, $Y_2O_2$, $Yb_2O_2$, etc., is blended as a stabilizer. Further, the diffusion regulation layer 63 is formed by a porous sintered body of alumina, magnesia, silica, spinel, mullite, or other heat resistant inorganic substances. Furthermore, the electrodes 55-58 is formed by platinum or other precious metal with a high catalytic activity.

Across the gas chamber side electrode 57 and the reference side electrode 58 of the reference cell 61, sensor applied voltage Vr is applied by the reference cell voltage application device 70 which is mounted in the ECU 31. In addition, the ECU 31 is provided with a reference cell output current detection device 71 which detects the reference cell output current Ir flowing across these electrodes 57, 58 through the second solid electrolyte layer 54 when the reference cell voltage application device 70 applies the sensor applied voltage Vr.

Further, between the gas chamber side electrode 55 and the exhaust side electrode 56 of the pump cell 60, pump voltage Vp is applied by a pump voltage application device 72 which is mounted in the ECU 31. The pump voltage Vp applied by the pump voltage application device 72 is set in accordance with the reference cell output current Ir detected by the reference cell output current detection device 71. Specifically, the pump voltage Vp is set in accordance with the difference between the reference cell output current Ir detected by the reference cell output current detection device 71 and the preset target current (for example, zero). In addition, the ECU 31 is provided with a pump current detection device 73 which detects a pump current Ip which flows across these electrodes 55 and 56 through the first solid electrolyte layer 53 when the pump voltage application device 72 applies the pump voltage Vp.

Note that, if the pump voltage application device 72 changes the pump voltage Vp, the pump current Ip which flows across the electrodes 55, 56 changes. In other words, the pump voltage application device 72 can be said to control the pump current Ip. Therefore, the pump voltage application device 72 acts as a pump current control device which controls the pump current Ip. Note that, the pump current Ip, for example, changes by arranging a variable resistor in series with the pump voltage application device 72 and changing this variable resistor. Therefore, as the pump current control device, a variable resistor or other means other than the pump voltage application device 72 may be used.

<Operation of Air-Fuel Ratio Sensor>

Figure 6:
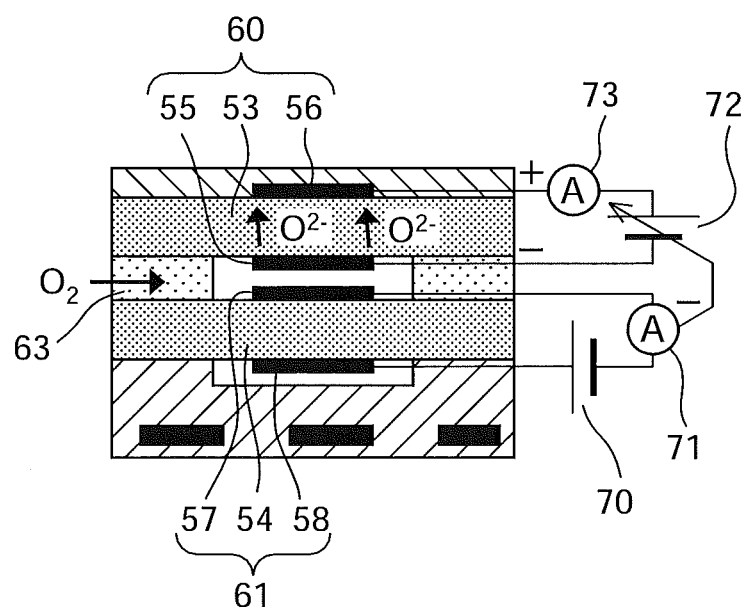
FIG. 6 is a view which schematically shows the operation of the air-fuel ratio sensor.
Figure 6:
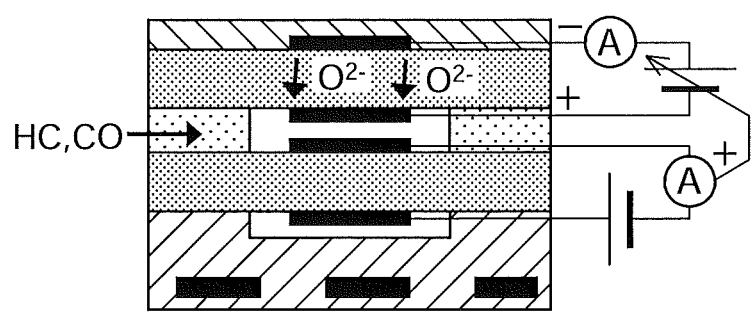
Figure 6:
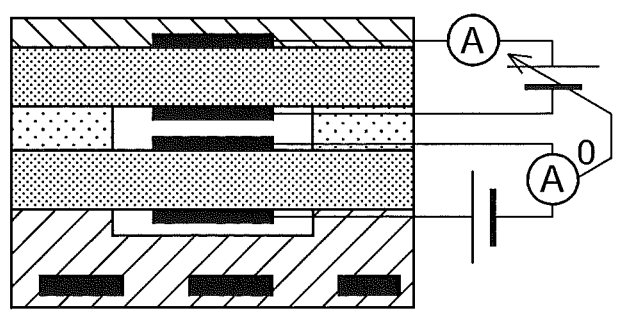

Next, referring to FIG. 6, the basic concept of the operation of the thus configured air-fuel ratio sensors 40, 41 will be explained. FIG. 6 is a view which schematically shows the operation of the air-fuel ratio sensors 40, 41. At the time of use, each of the air-fuel ratio sensors 40, 41 is arranged so that the protection layer 66 and the outer circumferential surface of the diffusion regulating layer 63 are exposed to the exhaust gas. Further, atmospheric air is introduced into the reference gas chamber 52 of the air-fuel ratio sensors 40, 41.

In the above-mentioned way, the solid electrolyte layers 53, 54 is formed by a sintered body of an oxygen ion conductive oxide. Therefore, it has the property of an electromotive force E being generated which makes oxygen ions move from the high concentration side surface side to the low concentration side surface side if a difference occurs in the oxygen concentration between the two side surfaces of the solid electrolyte layers 53, 54 in the state activated by the high temperature (oxygen cell characteristic).

Conversely, if a potential difference occurs between the two side surfaces, the solid electrolyte layers 53, 54 has the characteristic of trying to make the oxygen ions move so that a ratio of oxygen concentration occurs between the two side surfaces of the solid electrolyte layer in accordance with the potential difference (oxygen pump characteristic). Specifically, when a potential difference occurs across the two side surfaces, movement of oxygen ions is caused so that the oxygen concentration at the side surface which has a positive polarity becomes higher than the oxygen concentration at the side surface which has a negative polarity, by a ratio according to the potential difference.

Therefore, at the pump cell 60, if the pump voltage application device 72 applies the pump voltage Vp across the gas chamber side electrode 55 and the exhaust side electrode 56, movement of oxygen ions occurs corresponding to this. Along which such movement of oxygen ions, oxygen is pumped into or pumped out of the exhaust gas in the measured gas chamber 51.

On the other hand, in the reference cell 61 of the present embodiment, due to the properties of the second solid electrolyte layer 54 explained above, based on the later explained mechanism, when the exhaust air-fuel ratio in the measured gas chamber 51 is the stoichiometric air-fuel ratio, the reference cell output current which flows across the electrodes 57, 58 becomes zero. On the other hand, when the exhaust air-fuel ratio in the measured gas chamber 51 is a rich air-fuel ratio, the reference cell output current which flows across the electrodes 57, 58 becomes a negative current of a magnitude which is proportional to the difference from the stoichiometric air-fuel ratio. Conversely, when the exhaust air-fuel ratio in the measured gas chamber is the lean air-fuel ratio, the reference cell output current which flows across the electrodes 57, 58 becomes a positive current of a magnitude which is proportional to the difference from the stoichiometric air-fuel ratio.

When the exhaust air-fuel ratio around the air-fuel ratio sensors 40, 41 is leaner than the stoichiometric air-fuel ratio, as shown in FIG. 6(A), exhaust gas which has lean air-fuel ratio flows into measured gas chamber 51 through the diffusion regulating layer 63. If a lean air-fuel ratio exhaust gas containing such a large amount of oxygen flows in, by means of the mechanism mentioned below, a positive reference cell output current will flow across the electrodes 57 and 58 of the reference cell 61, proportional to the difference from the stoichiometric air-fuel ratio, and this reference cell output current will be detected by the reference cell output current detection device 71.

If the reference cell output current detection device 71 detects the reference cell output current, based on this current, the pump voltage application device 72 applies pump voltage to the electrodes 55 and 56 of the pump cell 60. In particular, if the reference cell output current detection device 71 detects a positive reference cell output current, pump voltage is applied using the exhaust side electrode 56 as the positive electrode and the gas chamber side electrode 855 as the negative electrode. By applying pump voltage to the electrodes 55, 56 of the pump cell 60 in this way, at the first solid electrolyte layer 53 of the pump cell 60, movement of oxygen ions will occur from the negative electrode to the positive electrode, that is, from the gas chamber side electrode 55 toward the exhaust side electrode 56. For this reason, the oxygen in the measured gas chamber 51 is pumped out into the exhaust gas around the air-fuel ratio sensors 40, 41.

The flow rate of oxygen pumped out from inside each measured gas chamber 51 to the exhaust gas around the air-fuel ratio sensors 40, 41 is proportional to the pump voltage. Further, the pump voltage is proportional to the magnitude of the positive reference cell output current detected by the reference cell output current detection device 71. Therefore, the larger the lean degree of the exhaust air-fuel ratio in the measured gas chamber 51, that is, the higher the concentration of oxygen in the measured gas chamber 51, the greater the flow rate of oxygen pumped out from the inside of the measured gas chamber 51 into the exhaust gas around the air-fuel ratio sensors 40, 41. As a result, the flow rate of oxygen flowing through the diffusion regulating layer 63 into the measured gas chamber 51 and the flow rate of oxygen pumped out by the pump cell 60 basically conform to each other. Therefore, the air-fuel ratio in the measured gas chamber 51, is basically maintained substantially at the stoichiometric air-fuel ratio.

The flow rate of oxygen pumped by the pump cell 60 equals the flow rate of oxygen ions which move through the inside of the first solid electrolyte layer 53 of the pump cell 60. Further, the flow rate of the oxygen ions is equal to the current which flows across the electrodes 55, 56 of the pump cell 60. Accordingly, by detecting the pump current flowing across the electrodes 55, 56, as an output current of the air-fuel ratio sensors 40, 41 (hereinafter, referred to as "sensor output current"), by the pump current detection device 73, it is possible to detect the flow rate of oxygen flowing through the diffusion regulating layer 63 into the measured gas chamber 51, and thus a lean air-fuel ratio of the exhaust gas around the measured gas chamber 51.

On the other hand, when the exhaust air-fuel ratio around the air-fuel ratio sensors 40, 41 is richer than the stoichiometric air-fuel ratio, as shown in FIG. 6(B), exhaust gas of rich air-fuel ratio will flow into the measured gas chamber 51 through the diffusion regulating layer 63. If the rich air-fuel ratio exhaust gas containing a large amount of unburned gas flows in like this way, across the electrodes 57 and 58 of the reference cell 61, a negative reference cell output current will flow proportional to the difference from the stoichiometric air-fuel ratio. This reference cell output current is detected by the reference cell output current detection device 71.

If the reference cell output current detection device 71 detects the reference cell output current, based on this current, a pump voltage is applied across the electrodes 55 and 56 of the pump cell 60 by the pump voltage application device 72, by the mechanism mentioned below. In particular, if the reference cell output current detection device 71 detects a negative reference cell output current, pump voltage is applied using the gas chamber side electrode 55 as the positive electrode and the exhaust side electrode 56 as the negative electrode. By applying the pump voltage in this way, in the first solid electrolyte layer 53 of the pump cell 60, movement of oxygen ions occurs from the negative electrode to the positive electrode, that is, from the exhaust side electrode 56 toward the gas chamber side electrode 55. For this reason, the oxygen in the exhaust gas around the air-fuel ratio sensors 40, 41 is pumped into the measured gas chamber 51.

The flow rate of oxygen pumped from the exhaust gas around the air-fuel ratio sensors 40, 41 into each measured gas chamber 51 is proportional to the pump voltage. Further, the pump voltage is proportional to the magnitude of the negative reference cell output current detected by the reference cell output current detection device 71. Therefore, the larger the rich degree of the exhaust air-fuel ratio in the measured gas chamber 51, that is, the higher the concentration of unburned gas in the measured gas chamber 51, the greater the flow rate of oxygen pumped into the measured gas chamber 51 from the exhaust gas around the air-fuel ratio sensors 40, 41. As a result, the flow rate of unburned gas flowing through the diffusion regulating layer 63 into the measured gas chamber 51 and the flow rate of oxygen pumped in by the pump cell 60 become a chemical equivalent ratio and, accordingly, the air-fuel ratio in of the measured gas chamber 51 is basically maintained at the stoichiometric air-fuel ratio.

The flow rate of oxygen pumped in by the pump cell 60 is equal to the flow rate of oxygen ions which move through the inside of the first solid electrolyte layer 53 in the pump cell 60. Further, this flow rate of oxygen ions is equal to the current which flows across the electrodes 55, 56 of the pump cell 60. Accordingly, by detecting the pump current flowing between the electrodes 55 and 56, as a sensor output current, by the pump current detection device 73, it is possible to detect the flow rate of unburned gas flowing through the diffusion regulating layer 63 into the measured gas chamber 51 and thus the rich air-fuel ratio of the exhaust gas around the measured gas chamber 51.

Further, when the exhaust air-fuel ratio around the air-fuel ratio sensors 40, 41 is the stoichiometric air-fuel ratio, as shown in FIG. 6(C), exhaust gas of the stoichiometric air-fuel ratio flows into the measured gas chamber 51 through the diffusion regulating layer 63. If exhaust gas of the stoichiometric air-fuel ratio flows in in this way, the reference cell output current flowing across the electrodes 57, 58 of the reference cell 61 becomes zero by the mechanism mentioned below, and the reference cell output current is detected by the reference cell output current detection device 71.

If the reference cell output current detected by the reference cell output current detection device 71 is zero, along with this, the pump voltage applied by the pump voltage application device 72 is also zero. Therefore, in the first solid electrolyte layer 53 of the pump cell 60, no movement of oxygen ions occurs, and accordingly the inside of the measured gas chamber 51 is basically held substantially at the stoichiometric air-fuel ratio. Further, no movement of oxygen ions occurs in the first solid electrolyte layer 53 of the pump cell 60, and therefore the pump current detected by the pump current detection device 73 also becomes zero. Therefore, when the pump current detected by the pump current detection device 73 is zero, it is learned that the air-fuel ratio of the exhaust gas around the measured gas chamber 51 is the stoichiometric air-fuel ratio.

Figure 7:
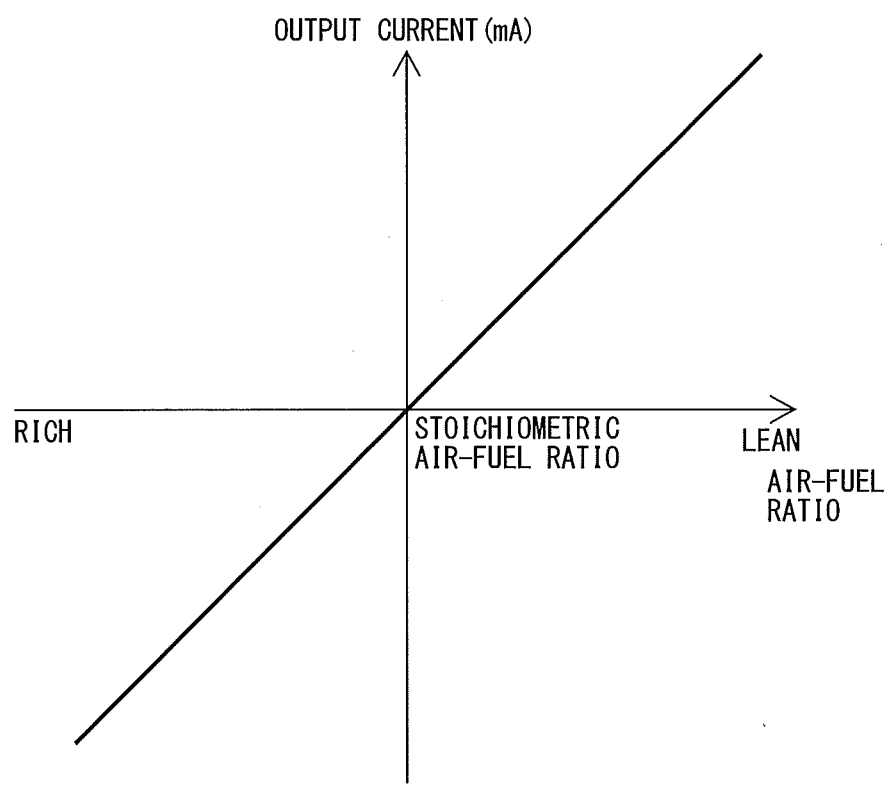
FIG. 7 is a view which shows an output characteristic of an air-fuel ratio sensor.

The thus configured air-fuel ratio sensors 40, 41 have the output characteristic shown in FIG. 7. That is, in the air-fuel ratio sensors 40, 41, the larger the exhaust air-fuel ratio becomes (that is, the leaner it becomes), the larger the pump current (sensor output current) Ip becomes. In addition, in the present embodiment, the air-fuel ratio sensors 40, 41 are configured so that the pump current (sensor output current) Ip becomes zero when the exhaust air-fuel ratio is the stoichiometric air-fuel ratio.

<Operation of Reference Cell>

Figure 8:
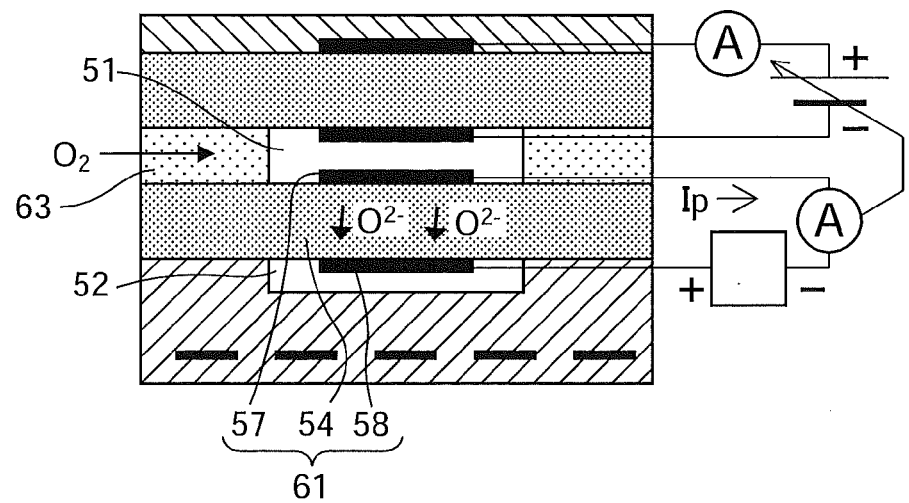
FIG. 8 is a view which schematically shows an operation of a reference cell.
Figure 8:
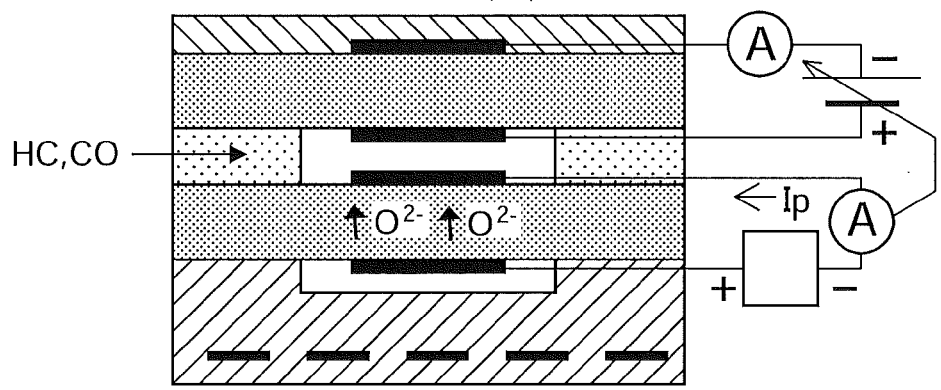
Figure 8:
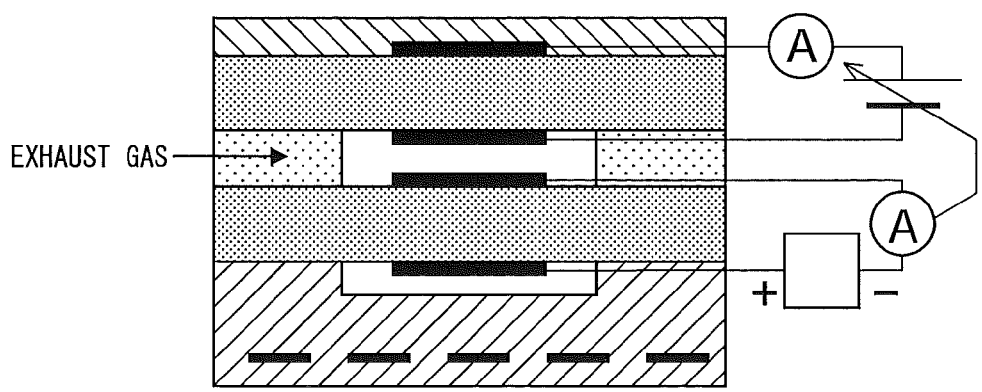

As explained above, in the reference cell 61, when the exhaust air-fuel ratio in the measured gas chamber 51 is a stoichiometric air-fuel ratio, the reference cell output current flowing across the electrodes 57 and 58 becomes zero, while when the exhaust air-fuel ratio in the measured gas chamber 51 becomes an air-fuel ratio which is different from the stoichiometric air-fuel ratio, the reference cell output current changes in accordance with the exhaust air-fuel ratio. Below, referring to FIG. 8, the basic concept of the operation of the reference cell 61 will be explained. FIG. 8 is a view which schematically shows the operation of the reference cell 61. At the time of use, as explained above, exhaust gas is introduced into the measured gas chamber 51 through a diffusion regulating layer 63, and atmospheric air is introduced into the reference gas chamber 52. Further, as shown in FIGS. 5 and 8, at the air-fuel ratio sensors 40, 41, a constant sensor applied voltage Vr is applied across these electrodes 57 and 58 so that the reference side electrode 58 becomes a positive polarity and the gas chamber side electrode 57 becomes a negative polarity. Note that in the present embodiment, the sensor applied voltages Vr in both of the air-fuel sensors 40 and 41 are the same voltage as each other.

When the exhaust air-fuel ratio in the measured gas chamber 51 is leaner than the stoichiometric air-fuel ratio, the ratio of concentration of oxygen between the two side surfaces of the second solid electrolyte layer 54 does not become that large. Therefore, if setting the sensor applied voltage Vr to a suitable value, between the two side surfaces of the second solid electrolyte layer 54, the actual ratio of concentration of oxygen becomes smaller than the ratio of concentration of oxygen which corresponds to the sensor applied voltage Vr. For this reason, as shown in FIG. 8(A), movement of oxygen ions occurs from the gas chamber side electrode 57 to the reference side electrode 58 so that the ratio of concentration of oxygen between the two side surfaces of the second solid electrolyte layer 54 becomes larger toward the ratio of concentration of oxygen which corresponds to the sensor applied voltage Vr. As a result, current flows from the positive electrode of the reference cell voltage application device 70 which applies the sensor applied voltage Vr, through the reference side electrode 58, second solid electrolyte layer 54, and gas chamber side electrode 57, to the negative electrode of the reference cell voltage application device 70.

The magnitude of the current (reference cell output current) Ir is proportional to the flow rate of oxygen flowing from the exhaust gas through the diffusion regulating layer 63 to the measured gas chamber 51, if setting the sensor applied voltage Vr to a suitable value. Therefore, by detecting the magnitude of this current Ir by the reference cell output current detection device 71, the concentration of oxygen in the measured gas chamber 51 can be learned and, in turn, the air-fuel ratio at the lean region can be learned.

On the other hand, when the exhaust air-fuel ratio in the measured gas chamber 51 is richer than the stoichiometric air-fuel ratio, the unburned gas flows from the exhaust gas through the diffusion regulating layer 63 into the measured gas chamber 51, and therefore even if oxygen is present on the gas chamber side electrode 57, it is removed by reaction with the unburned gas. Therefore, in the measured gas chamber 51, the concentration of oxygen becomes extremely low and, as a result, the ratio of the concentration of oxygen at the two side surfaces of the second solid electrolyte layer 54 becomes large. For this reason, if setting the sensor applied voltage Vr to a suitable value, between the two side surfaces of the second solid electrolyte layer 54, the actual ratio of concentration of oxygen becomes larger compared with the ratio of concentration of oxygen corresponding to the sensor applied voltage Vr. Therefore, as shown in FIG. 8(B), movement of oxygen ions occurs from the reference side electrode 58 toward the gas chamber side electrode 57 so that the ratio of concentration of oxygen between the two side surfaces of the second solid electrolyte layer 54 becomes smaller toward the ratio of concentration of oxygen which corresponds to the sensor applied voltage Vr. As a result, current flows from the reference side electrode 58, through the reference cell voltage application device 70 which applies the sensor applied voltage Vr, to the gas chamber side electrode 57.

The magnitude of the current (reference cell output current) Ir which flows at this time, if setting the sensor applied voltage Vr to a suitable value, is determined by the flow rate of oxygen ions which moves through the second solid electrolyte layer 54 from the reference side electrode 58 to the gas chamber side electrode 57. The oxygen ions react (burn) on the gas chamber side electrode 57 with the inflowing unburned gas, which flows from the exhaust gas through the diffusion regulating layer 63 and are diffused into the measured gas chamber 51. Accordingly, the flow rate of movement of oxygen ions corresponds to the concentration of unburned gas in the exhaust gas which flows into the measured gas chamber 51. Therefore, by detecting the magnitude of this current Ir by the reference cell output current detection device 71, it is possible to learn the concentration of unburned gas in the measured gas chamber 51 and in turn possible to learn the air-fuel ratio in the rich region.

Further, when the exhaust air-fuel ratio in the measured gas chamber 51 is the stoichiometric air-fuel ratio, the amounts of oxygen and unburned gas in the measured gas chamber 51 become a chemical equivalent ratio. Therefore, the catalytic action of the gas chamber side electrode 57 causes the oxygen and unburned gas to completely burn, and no fluctuation occurs in the concentrations of oxygen and unburned gas in the measured gas chamber 51. As a result, the ratio of concentration of oxygen between the two side surfaces of the second solid electrolyte layer 54, does not fluctuate, but is maintained as the ratio of concentration of oxygen which corresponds to the sensor applied voltage Vr. Therefore, as shown in FIG. 8(C), no movement of oxygen ions occurs due to the oxygen pump characteristic, and as a result, no current is generated which flows through the circuit.

<Action and Effect of Air-Fuel Ratio Sensors>

Figure 9:
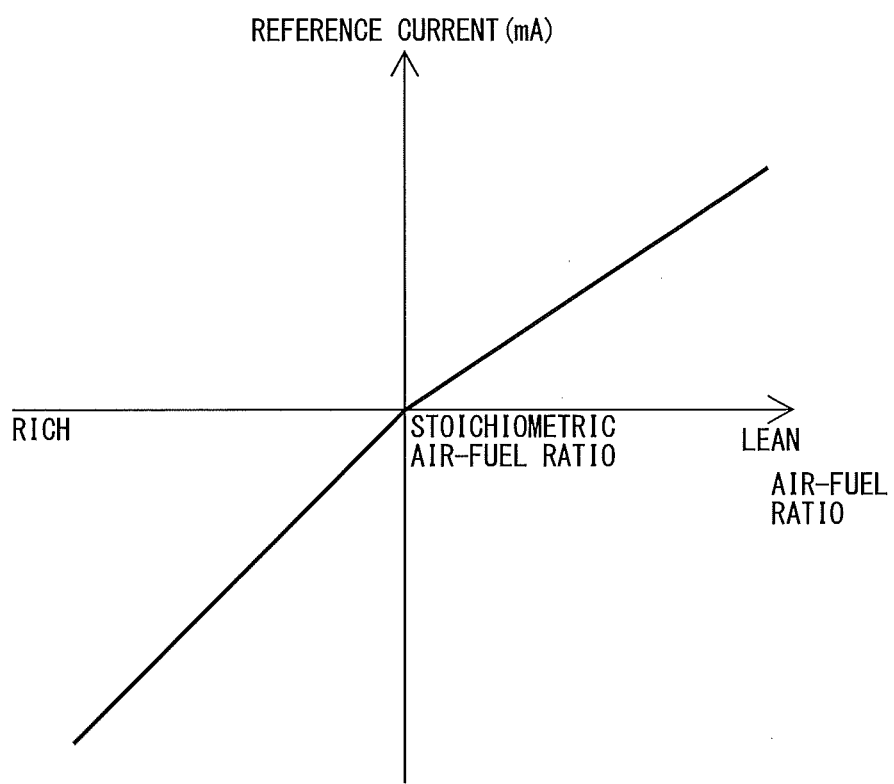
FIG. 9 is a view which shows an output characteristic of a reference cell.

Such a configured reference cell 61 has the output characteristic shown in FIG. 9. That is, in the reference cell 61, the larger the exhaust air-fuel ratio becomes (that is, the leaner it becomes), the larger the reference cell output current Ir becomes. In addition, the reference cell 61 is configured so that the reference cell output current Ir becomes zero when the exhaust air-fuel ratio is the stoichiometric air-fuel ratio.

Further, in the reference cell 61, the sensor applied voltage Vr is applied across the electrodes 57 and 58, and therefore the oxidation reaction or reduction reaction is forcibly performed on the gas chamber side electrode 57 and reference side electrode 58. Therefore, both when the air-fuel ratio of the exhaust gas flowing into the measured gas chamber 51 changes from a rich air-fuel ratio to a lean air-fuel ratio and when it changes from a lean air-fuel ratio to a rich air-fuel ratio, if the exhaust gas in the measured gas chamber 51 is the same, the reference cell output current Ir which flows across the electrodes 57 and 58 becomes the same. As a result, there is no problem of hysteresis which occurred in the conventional double-cell type air-fuel ratio sensor.

In addition, in the reference cell 61, sensor applied voltage Vr is applied across the electrodes 57 and 58, and therefore the reaction at the gas chamber side electrode 57 is promoted and accordingly the ingredients in the exhaust gas are forcibly oxidized or reduced regardless of their reactivity. Therefore, the oxidation reaction and reduction reaction on the gas chamber side electrode 57 is less likely to be affected by the composition of ingredients contained in the exhaust gas. Even different ingredients in the exhaust gas react with substantially the same responses. As a result, the problems relating to the response due to the composition of ingredients in the exhaust gas, which used to occur in conventional double-cell type air-fuel ratio sensors, do not arise.

That is, according to the air-fuel ratio sensors 40, 41 of the present embodiment, it is possible to solve the problems occurred in the conventional double-cell type air-fuel ratio sensors. In addition, since the air-fuel ratio sensors 40, 41 of the present embodiment are double-cell type of air-fuel ratio sensors, the problems such as occurred in the conventional single-cell type air-fuel ratio sensors do not arise. That is, in the air-fuel ratio sensors 40, 41, there is no change in output current due to changes in the internal resistance accompanying aging. Further, the air-fuel ratio can be detected over a broad range. Therefore, according to the air-fuel ratio sensors 40, 41 of the present embodiment, it is possible to overcome all of the defects which occurred in the conventional single-cell type of air-fuel ratio sensors and double-cell type of air-fuel ratio sensors.

<Circuits of Voltage Application Device and Current Detection Device>

Figure 10:
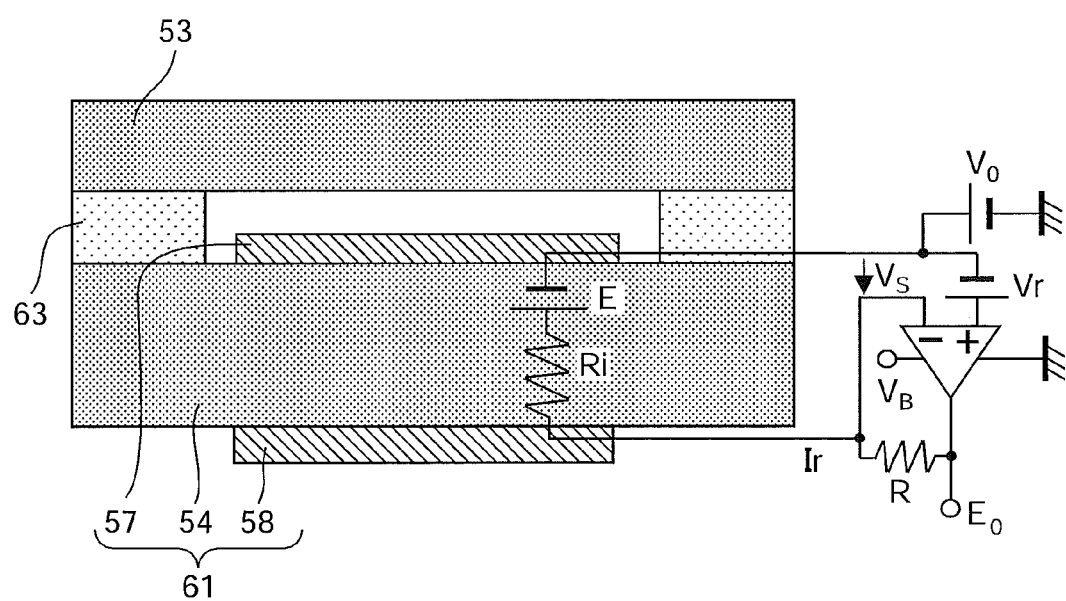
FIG. 10 is a view which shows one example of a specific circuit which forms a reference cell voltage application device and a reference cell output current detection device.

FIG. 10 shows an example of the specific circuits which form the reference cell voltage application device 70 and reference cell current detection device 71. In the illustrated example, the electromotive force E which occurs due to the oxygen cell characteristic is expressed as "E", the internal resistance of the second solid electrolyte layer 54 is expressed as "Ri", and the difference of electrical potential across the two electrodes 57, 58 is expressed as "Vs".

As will be understood from FIG. 10, the reference cell voltage application device 70 basically performs negative feedback control so that the electromotive force E which occurs due to the oxygen cell characteristic matches the sensor applied voltage Vr. In other words, the reference cell voltage application device 70 performs negative feedback control so that even when a change in the oxygen concentration ratio between the two side surfaces of the second solid electrode layer 54 causes the potential difference Vs between the two electrodes 57 and 58 to change, this potential difference Vs becomes the sensor applied voltage Vr.

Therefore, when the exhaust air-fuel ratio in the measured gas chamber 51 becomes the stoichiometric air-fuel ratio and no change occurs in the oxygen concentration ratio between the two side surfaces of the second solid electrolyte layer 54, the oxygen concentration ratio between the two side surfaces of the second solid electrolyte layer 54 becomes the oxygen concentration ratio corresponding to the sensor applied voltage Vr. In this case, the electromotive force E conforms to the sensor applied voltage Vr, the potential difference Vs between the two electrodes 57 and 58 also becomes the sensor applied voltage Vr, and, as a result, the current Ir does not flow.

On the other hand, when the exhaust air-fuel ratio becomes an air-fuel ratio which is different from the stoichiometric air-fuel ratio and a change occurs in the oxygen concentration ratio between the two side surfaces of the second solid electrolyte layer 54, the oxygen concentration ratio between the two side surfaces of the second solid electrolyte layer 54 does not become an oxygen concentration ratio corresponding to the sensor applied voltage Vr. In this case, the electromotive force E becomes a value different from the sensor applied voltage Vr. Therefore, due to negative feedback control, a potential difference Vs is applied between the two electrodes 57 and 58 so that oxygen ions move between the two side surfaces of the second solid electrolyte layer 54 so that the electromotive force E conforms to the sensor applied voltage Vr. Further, current Ir flows along with movement of oxygen ions at this time. As a result, the electromotive force E converges to the sensor applied voltage Vr. If the electromotive force E converges to the sensor applied voltage Vr, finally the potential difference Vs also converges to the sensor applied voltage Vr.

Therefore, the reference cell voltage application device 70 can be said to substantially apply the sensor applied voltage Vr between the two electrodes 57 and 58. Note that, the electrical circuit of the reference cell voltage application device 70 does not have to be one such as shown in FIG. 10. The circuit may be any form of device so long as able to substantially apply the sensor applied voltage Vr across the two electrodes 57, 58.

Further, the reference cell current detection device 71 does not actually detect the current. It detects the voltage $E_0$ to calculate the current from this voltage $E_0$. In this regard, $E_0$ is expressed as in the following equation (1).

$$E_0 = Vr + V_0 + I_r R \qquad (1)$$

wherein, $V_0$ is the offset voltage (voltage applied so that $E_0$ does not become a negative value, for example, 3V), while R is the value of the resistance shown in FIG. 10.

In equation (1), the sensor applied voltage Vr, offset voltage $V_0$, and resistance value R are constant, and therefore the voltage $E_0$ changes in accordance with the current Ir. For this reason, if detecting the voltage $E_0$, it is possible to calculate the current Ir from that voltage $E_0$.

Therefore, the reference cell current detection device 71 can be said to substantially detect the current Ir which flows across the two electrodes 57, 58. Note that, the electrical circuit of the reference cell current detection device 71 does not have to be one such as shown in FIG. 10. If possible to detect the current Ir flowing across the two electrodes 57, 58, any form of device may be used.

<Summary of Control of Air-Fuel Ratio>

Next, a summary of the air-fuel ratio control, which is performed, by using the air-fuel ratio sensors 40 and 41 mentioned above, in a control system of an internal combustion engine of the present invention, will be explained. In the present embodiment, based on the sensor output current Ipup of the upstream side air-fuel ratio sensor 40, feedback control is performed so that the sensor output current (that is, the air-fuel ratio of the exhaust gas flowing into the upstream side exhaust purification catalyst 20) Ipup of the upstream side air-fuel ratio sensor 40 becomes a value corresponding to the target air-fuel ratio.

The target air-fuel ratio of the exhaust gas flowing into the upstream side exhaust purification catalyst 20 is set based on the sensor output current Ipdwn of the downstream side air-fuel ratio sensor 41. Specifically, the target air-fuel ratio is set to the lean set air-fuel ratio when the sensor output current Ipdwn of the downstream side air-fuel ratio sensor 41 becomes the rich judgement reference value Iref or less, and is maintained at that air-fuel ratio. In this regard, the rich judgement reference value Iref is a value corresponding to a predetermined rich judged air-fuel ratio (for example, 14.55), which is slightly richer than the stoichiometric air-fuel ratio. Further, the lean set air-fuel ratio is a predetermined air-fuel ratio leaner than the stoichiometric air-fuel ratio by a certain extent. For example, it is 14.65 to 20, preferably 14.68 to 18, more preferably 14.7 to 16 or so.

If the target air-fuel ratio is changed to the lean set air-fuel ratio, the oxygen storage amount OSAsc of the upstream side exhaust purification catalyst 20 is estimated. The oxygen storage amount OSAsc is estimated based on the sensor output current Ipup of the upstream side air-fuel ratio sensor 40, and the estimated value of the amount of intake air to the combustion chamber 5, which is calculated based on the air flow meter 39, etc., or the amount of fuel injection from the fuel injector 11, etc. Further, if the estimated value of the oxygen storage amount OSAsc becomes a predetermined judged reference storage amount Cref or more, the target air-fuel ratio which was the lean set air-fuel ratio up to then is changed to a slight rich set air-fuel ratio and is maintained at that air-fuel ratio. The slight rich set air-fuel ratio is a predetermined air-fuel ratio slightly richer than the stoichiometric air-fuel ratio. For example, it is 13.5 to 14.58, preferably 14 to 14.57, more preferably 14.3 to 14.55 or so. After that, when the sensor output current Ipdwn of the downstream side air-fuel ratio sensor 41 again becomes the rich judgement reference value Iref or less, the target air-fuel ratio is again set to the lean set air-fuel ratio, and then a similar operation is repeated.

In this way, in the present embodiment, the target air-fuel ratio of the exhaust gas flowing into the upstream side exhaust purification catalyst 20 is alternately set to the lean set air-fuel ratio and the slight rich set air-fuel ratio. In particular, in the present embodiment, the difference between the lean set air-fuel ratio and the stoichiometric air-fuel ratio is larger than the difference between the slight rich set air-fuel ratio and the stoichiometric air-fuel ratio. Therefore, in the present embodiment, the target air-fuel ratio is alternately set to lean set air-fuel ratio for a short period of time and slight rich set air-fuel ratio for a long period of time.

<Explanation of Control Using Time Chart>

Figure 11:
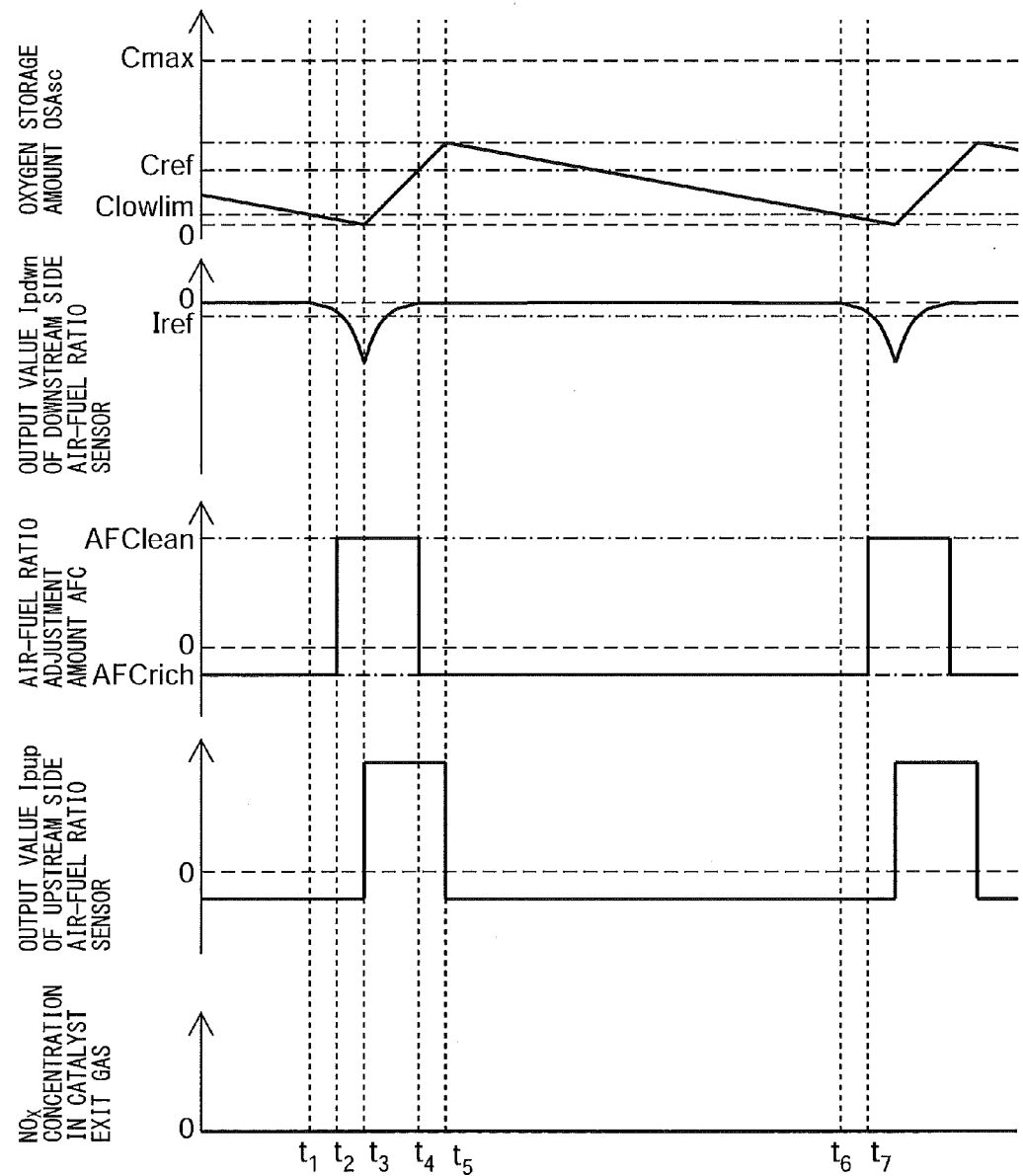
FIG. 11 is a time chart of an oxygen storage amount of an upstream side exhaust purification catalyst, etc.
Figure 15:
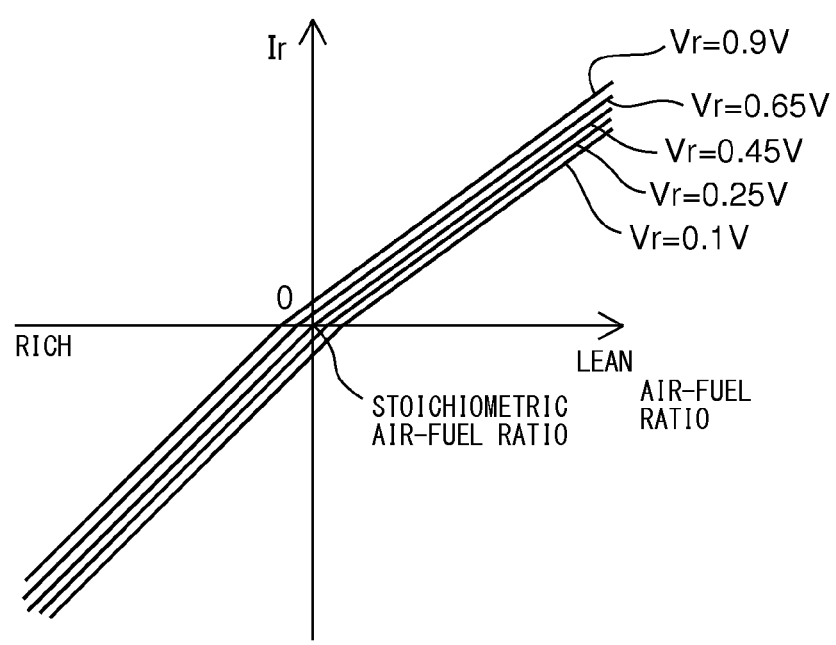
FIG. 15 is a view which shows a relationship between an exhaust air-fuel ratio and a reference cell output current.

Referring to FIG. 11, the above-mentioned such operation will be explained in detail. FIG. 15 is a time chart of the oxygen storage amount OSAsc of the upstream side exhaust purification catalyst 20, the sensor output current Ipdwn of the downstream side air-fuel ratio sensor 41, the sensor output current Ipup of the upstream side air-fuel ratio sensor 40 and NOx concentration in the exhaust gas flowing out from the upstream side exhaust purification catalyst 20, in the case of performing air-fuel ratio control in a control system of an internal combustion engine of the present invention.

Note that, the sensor output current Ipup of the upstream side air-fuel ratio sensor 40 becomes zero when the air-fuel ratio of the exhaust gas flowing into the upstream side exhaust purification catalyst 20 is the stoichiometric air-fuel ratio, becomes a negative value when the air-fuel ratio of the exhaust gas is a rich air-fuel ratio, and becomes a positive value when the air-fuel ratio of the exhaust gas is a lean air-fuel ratio. Further, when the air-fuel ratio of the exhaust gas flowing into the upstream side exhaust purification catalyst 20 is a rich air-fuel ratio or lean air-fuel ratio, the greater the difference from the stoichiometric air-fuel ratio, the larger the absolute value of the sensor output current Ipup of the upstream side air-fuel ratio sensor 40. The sensor output current Ipdwn of the downstream side air-fuel ratio sensor 41 also changes, similarly to the sensor output current Ipup of the upstream side air-fuel ratio sensor 40, depending on the air-fuel ratio of the exhaust gas flowing out from the upstream side exhaust purification catalyst 20. Further, the air-fuel ratio adjustment amount AFC is an adjustment amount relating to the target air-fuel ratio of the exhaust gas flowing into the upstream side exhaust purification catalyst 20. When the air-fuel ratio adjustment amount AFC is 0, the target air-fuel ratio is the stoichiometric air-fuel ratio, when the air-fuel ratio adjustment amount AFC is a positive value, the target air-fuel ratio becomes a lean air-fuel ratio, and when the air-fuel ratio adjustment amount AFC is a negative value, the target air-fuel ratio becomes a rich air-fuel ratio.

In the illustrated example, in the state before the time $t_1$, the air-fuel ratio adjustment amount AFC is set to the slight rich set adjustment amount AFCrich. The slight rich set adjustment amount AFCrich is a value corresponding to the slight rich set air-fuel ratio and a value smaller than 0. Therefore, the target air-fuel ratio is set to a rich air-fuel ratio. Along with this, the sensor output current Ipup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. However, the unburned gas contained in the exhaust gas is purified at the upstream side exhaust purification catalyst 20, and therefore the sensor output current Ipdwn of the downstream side air-fuel ratio sensor becomes substantially zero (corresponding to the stoichiometric air-fuel ratio). At this time, the air-fuel ratio of the exhaust gas flowing into the upstream side exhaust purification catalyst 20 becomes a rich air-fuel ratio, and therefore the amount of $NO_X$ exhausted from the upstream side exhaust purification catalyst 20 is suppressed.

If the oxygen storage amount OSAsc of the upstream side exhaust purification catalyst 20 gradually decreases, the oxygen storage amount OSAsc decreases to less than the lower limit storage amount at the time $t_1$. If the oxygen storage amount OSAsc decreases to less than the lower limit storage amount, part of the unburned gas flowing into the upstream side exhaust purification catalyst 20 flows out without being purified at the upstream side exhaust purification catalyst 20. For this reason, after the time the sensor output current Ipdwn of the downstream side air-fuel ratio sensor 41 gradually falls along with the decrease in the oxygen storage amount OSAsc of the upstream side exhaust purification catalyst 20. At this time as well, the air-fuel ratio of the exhaust gas flowing into the upstream side exhaust purification catalyst 20 becomes a rich air-fuel ratio, and therefore the amount of $NO_X$ exhausted from the upstream side exhaust purification catalyst 20 is suppressed.

Then, at the time $t_2$, the sensor output current Ipdwn of the downstream side air-fuel ratio sensor 41 reaches the rich judgement reference value Iref corresponding to the rich judged air-fuel ratio. In the present embodiment, if the sensor output current Ipdwn of the downstream side air-fuel ratio sensor 41 reaches the rich judgement reference value Iref, the air-fuel ratio adjustment amount AFC is switched to the lean set adjustment amount AFClean so as to suppress the decrease of the oxygen storage amount OSAsc of the upstream side exhaust purification catalyst 20. The lean set adjustment amount AFClean is a value corresponding to the lean set air-fuel ratio and is a value larger than 0. Therefore, the target air-fuel ratio is set to a lean air-fuel ratio.

Note that, in the present embodiment, the air-fuel ratio adjustment amount AFC is switched after the sensor output current Ipdwn of the downstream side air-fuel ratio sensor 41 reaches the rich judgement reference value Iref, that is, after the air-fuel ratio of the exhaust gas flowing out from the upstream side exhaust purification catalyst 20 reaches the rich judged air-fuel ratio which is slightly richer than the stoichiometric air-fuel ratio. This is because even if the oxygen storage amount of the upstream side exhaust purification catalyst 20 is sufficient, the air-fuel ratio of the exhaust gas flowing out from the upstream side exhaust purification catalyst 20 sometimes deviates slightly from the stoichiometric air-fuel ratio. That is, if it is judged that the oxygen storage amount has decreased to less than the lower limit storage amount when the sensor output current Ipdwn deviates slightly from zero (corresponding to the stoichiometric air-fuel ratio), even if there is actually a sufficient oxygen storage amount, there is a possibility that it is judged that the oxygen storage amount decreases to lower than the lower limit storage amount. Therefore, in the present embodiment, it is judged the oxygen storage amount decreases lower than the lower limit storage amount, only when the air-fuel ratio of the exhaust gas flowing out from the upstream side exhaust purification catalyst 20 reaches the rich judged air-fuel ratio. Conversely speaking, the rich judged air-fuel ratio is set to an air-fuel ratio which the air-fuel ratio of the exhaust gas flowing out from the upstream side exhaust purification catalyst 20 does not reach much at all when the oxygen storage amount of the upstream side exhaust purification catalyst 20 is sufficient.

Even if, at the time $t_2$, the target air-fuel ratio is switched to the lean air-fuel ratio, the air-fuel ratio of the exhaust gas flowing into the upstream side exhaust purification catalyst 20 does not immediately become the lean air-fuel ratio, and a certain extent of delay arises. As a result, the air-fuel ratio of the exhaust gas flowing into the upstream side exhaust purification catalyst 20 changes from the rich air-fuel ratio to the lean air-fuel ratio at the time $t_3$. Note that, during the times $t_2$ to $t_3$, the air-fuel ratio of the exhaust gas flowing out from the upstream side exhaust purification catalyst 20 is a rich air-fuel ratio, and therefore this exhaust gas contains unburned gas. However, the amount of discharge of $NO_X$ from the upstream side exhaust purification catalyst 20 is suppressed.

At the time $t_3$, if the air-fuel ratio of the exhaust gas flowing into the upstream side exhaust purification catalyst 20 changes to the lean air-fuel ratio, the oxygen storage amount OSAsc of the upstream side exhaust purification catalyst 20 increases. Further, along with this, the air-fuel ratio of the exhaust gas flowing out from the upstream side exhaust purification catalyst 20 changes to the stoichiometric air-fuel ratio, and the sensor output current Ipdwn of the downstream side air-fuel ratio sensor 41 also converges to zero. Although the air-fuel ratio of the exhaust gas flowing into the upstream side exhaust purification catalyst 20 is a lean air-fuel ratio at this time, the upstream side exhaust purification catalyst 20 has sufficient leeway in the oxygen storage ability, and therefore the oxygen in the inflowing exhaust gas is stored in the upstream side exhaust purification catalyst 20 and the $NO_X$ is reduced and purified. For this reason, the amount of $NO_X$ exhausted from the upstream side exhaust purification catalyst 20 is suppressed.

Then, if the oxygen storage amount OSAsc of the upstream side exhaust purification catalyst 20 increases, at the time $t_4$, the oxygen storage amount OSAsc reaches the judged reference storage amount Cref. In the present embodiment, if the oxygen storage amount OSAsc becomes the judged reference storage amount Cref, the air-fuel ratio adjustment amount AFC is switched to a slight rich set adjustment amount AFCrich (value smaller than 0) to stop the storage of oxygen in the upstream side exhaust purification catalyst 20. Therefore, the target air-fuel ratio is set to the rich air-fuel ratio.

However, as explained above, a delay occurs from when the target air-fuel ratio is switched to when the air-fuel ratio of the exhaust gas flowing into the upstream side exhaust purification catalyst 20 actually changes. For this reason, even if switching at the time $t_4$, after a certain extent of time passes from it, at the time $t_5$, the air-fuel ratio of the exhaust gas flowing into the upstream side exhaust purification catalyst 20 changes from the lean air-fuel ratio to the rich air-fuel ratio. During the times t4 to t5, the air-fuel ratio of the exhaust gas flowing into the upstream side exhaust purification catalyst 20 is the lean air-fuel ratio, and therefore the oxygen storage amount OSAsc of the upstream side exhaust purification catalyst 20 increases.

However, the judged reference storage amount Cref is set sufficiently lower than the maximum oxygen storage amount Cmax or the upper limit storage amount, and therefore even at the time $t_5$, the oxygen storage amount OSAsc does not reach the maximum oxygen storage amount Cmax or the upper limit storage amount. Conversely speaking, the judged reference storage amount Cref is set to an amount sufficiently small so that the oxygen storage amount OSAsc does not reach the maximum oxygen storage amount Cmax or the upper limit storage amount even if a delay occurs from when switching the target air-fuel ratio to when the air-fuel ratio of the exhaust gas flowing into the upstream side exhaust purification catalyst 20 actually changes. For example, the judged reference storage amount Cref is set to ¾ or less of the maximum oxygen storage amount Cmax, preferably ½ or less, more preferably ⅕ or less. Therefore, during times $t_4$ to $t_5$ as well, the amount of $NO_X$ exhausted from the upstream side exhaust purification catalyst 20 is suppressed.

After the time $t_5$, the air-fuel ratio adjustment amount AFC is set to the slight rich set adjustment amount AFCrich. Therefore, the target air-fuel ratio is set to the rich air-fuel ratio. Along with this, the sensor output current Ipup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. At the time $t_6$, in the same way as the time $t_1$, the oxygen storage amount OSAsc decreases below the lower limit storage amount. At this time as well, the air-fuel ratio of the exhaust gas flowing into the upstream side exhaust purification catalyst 20 becomes a rich air-fuel ratio, and therefore the amount of $NO_X$ exhausted from the upstream side exhaust purification catalyst 20 is suppressed.

Next, at the time $t_7$, in the same way as the time $t_2$, the sensor output current Ipdwn of the downstream side air-fuel ratio sensor 41 reaches the rich judgement reference value Iref corresponding to the rich judged air-fuel ratio. Due to this, the air-fuel ratio adjustment amount AFC is switched to the value AFClean corresponding to the lean set air-fuel ratio. Then, the cycle of the above-mentioned times $t_1$ to $t_6$ is repeated. Note that, during these cycles, the applied voltage Vrdwn to the downstream side air-fuel ratio sensor 41 is maintained at a voltage whereby the exhaust air-fuel ratio at the time of zero current becomes the rich judged air-fuel ratio.

Note that, such control of the air-fuel ratio adjustment amount AFC is performed by the ECU 31. Therefore, the ECU 31 can be said to comprise: an oxygen storage amount increasing means for continuously or intermittently setting a target air-fuel ratio of exhaust gas flowing into the upstream side catalyst 20 a lean set air-fuel ratio when the air-fuel ratio of the exhaust gas which was detected by the downstream side air-fuel ratio sensor 41 becomes a rich judged air-fuel ratio or less, until the oxygen storage amount OSAsc of the upstream side catalyst 20 becomes the judged reference storage amount Cref; and an oxygen storage amount decreasing means for continuously or intermittently setting the target air-fuel ratio a slight rich set air-fuel ratio when the oxygen storage amount OSAsc of the upstream side catalyst 20 becomes the judged reference storage amount Cref or more so that the oxygen storage amount OSAsc never exceeds the maximum oxygen storage amount Cmax but decreases toward zero.

As will be understood from the above explanation, according to the above embodiment, it is possible to constantly suppress the amount of discharge of $NO_X$ from the upstream side exhaust purification catalyst 20. That is, so long as performing the above-mentioned control, basically the amount of discharge of $NO_X$ from the upstream side exhaust purification catalyst 20 is small.

Further, in general, if the oxygen storage amount OSAsc is estimated based on the sensor output current Ipup of the upstream side air-fuel ratio sensor 40 and the estimated value of the intake air amount, etc., there is the possibility that error will occur. In the present embodiment as well, the oxygen storage amount OSAsc is estimated over the times $t_3$ to $t_4$, and therefore the estimated value of the oxygen storage amount OSAsc includes some error. However, even if such error is included, if setting the judged reference storage amount Cref sufficiently lower than the maximum oxygen storage amount Cmax or upper limit storage amount, the actual oxygen storage amount OSAsc will almost never reach the maximum oxygen storage amount Cmax or upper limit storage amount. Therefore, from such a viewpoint as well, it is possible to suppress the amount of discharge of $NO_X$ from the upstream side exhaust purification catalyst 20.

Further, if the oxygen storage amount of the exhaust purification catalyst is maintained constant, the oxygen storage ability of the exhaust purification catalyst will fall. As opposed to this, according to the present embodiment, the oxygen storage amount OSAsc constantly fluctuates up and down, so the oxygen storage ability is kept from falling.

Note that, in the above embodiment, during the times $t_2$ to $t_4$, the air-fuel ratio adjustment amount AFC is maintained at the lean set adjustment amount AFClean. However, in such a time period, the air-fuel ratio adjustment amount AFC does not necessarily have to be maintained constant. It may be set to gradually decrease or otherwise change. Similarly, during the times $t_4$ to $t_7$, the air-fuel ratio adjustment amount AFC is maintained at the weak rich set adjustment amount AFrich. However, in such a time period, the air-fuel ratio adjustment amount AFC does not necessarily have to be maintained constant. It may be set to gradually decrease or otherwise change.

However, even in this case, the air-fuel ratio adjustment amount AFC during the times $t_2$ to $t_4$ is set so that the difference of the average value of the target air-fuel ratio and the stoichiometric air-fuel ratio in that period becomes larger than the difference between the average value of the target air-fuel ratio and the stoichiometric air-fuel ratio during the times $t_4$ to $t_7$.

Further, in the above embodiment, the oxygen storage amount OSAsc of the upstream side exhaust purification catalyst 20 is estimated, based on the sensor output current Ipup of the upstream side air-fuel ratio sensor 40 and the estimated value of the amount of intake air to the combustion chamber 5, etc. However, the oxygen storage amount OSAsc may also be calculated by other parameters in addition to these parameters and may be estimated based on parameters which are different from these parameters. Further, in the above embodiment, if the estimated value of the oxygen storage amount OSAsc becomes the judged reference storage amount Cref or more, the target air-fuel ratio is switched from the lean set air-fuel ratio to the weak rich set air-fuel ratio. However, the timing of switching the target air-fuel ratio from the lean set air-fuel ratio to the weak rich set air-fuel ratio may, for example, use as a reference other parameter, such as the engine operating time etc. from when switching the target air-fuel ratio from the weak rich set air-fuel ratio to the lean set air-fuel ratio. However, even in this case, the target air-fuel ratio has to be switched from the lean set air-fuel ratio to the weak rich set air-fuel ratio in the period when the oxygen storage amount OSAsc of the upstream side exhaust purification catalyst 20 is estimated to be smaller than the maximum oxygen storage amount.

Note that in the above embodiment, during the times $t_4$ to $t_7$, the air-fuel ratio adjustment amount AFC is fixed at the slight rich set adjustment amount AFCrich, but even during this period, the air-fuel ratio adjustment amount AFC may temporarily be set to the stoichiometric air-fuel ratio or lean air-fuel ratio. In the same way, in the above embodiment, during the times $t_1$ to $t_4$, the air-fuel ratio adjustment amount AFC is fixed at the lean set adjustment amount AFClean, but even during this period, the air-fuel ratio adjustment amount AFC may temporarily be set to the stoichiometric air-fuel ratio or rich air-fuel ratio.

<Explanation of Specific Control>

Figure 12:
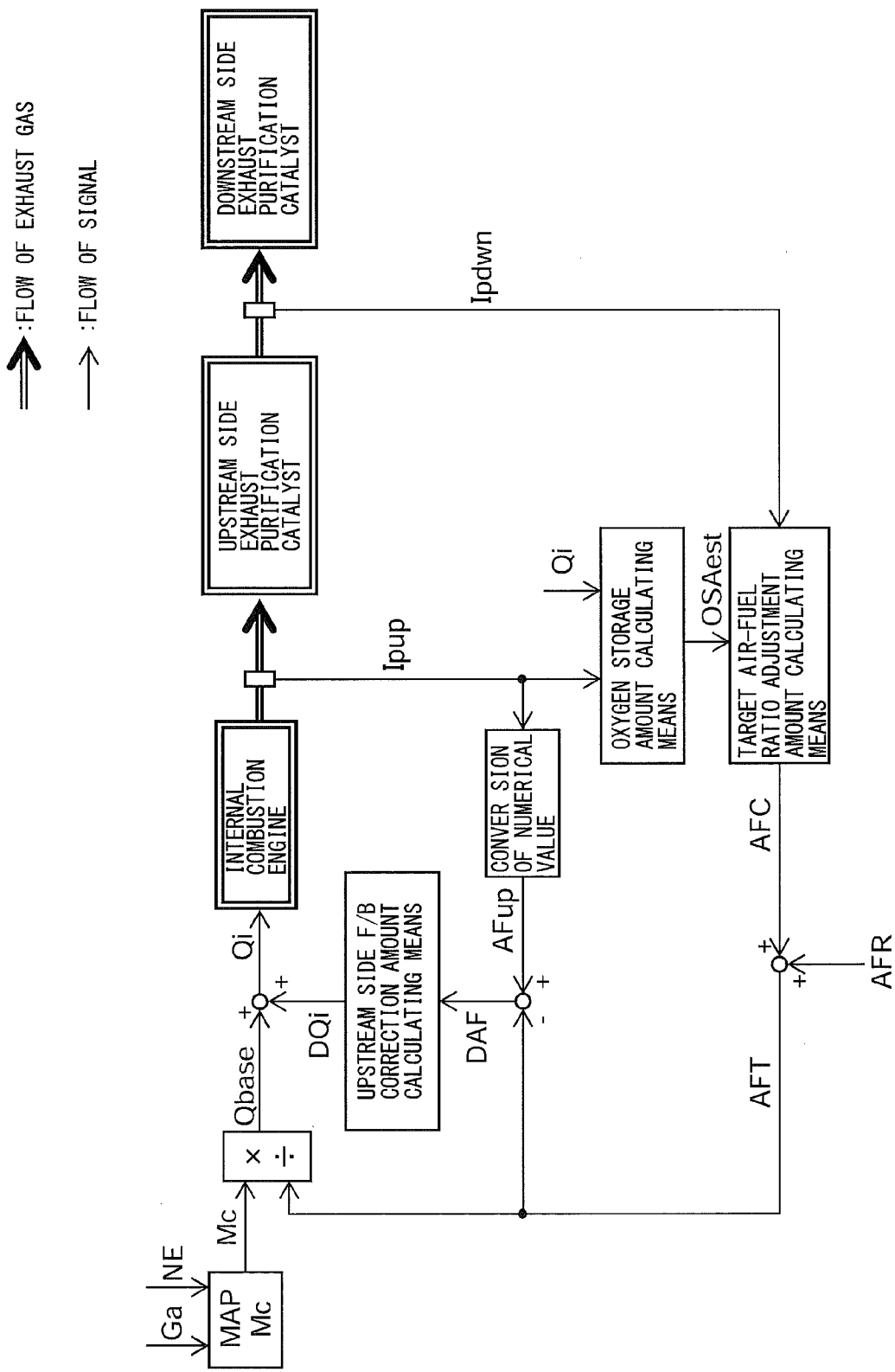
FIG. 12 is a view which shows functional blocks in the control system of the present invention.
Figure 13:
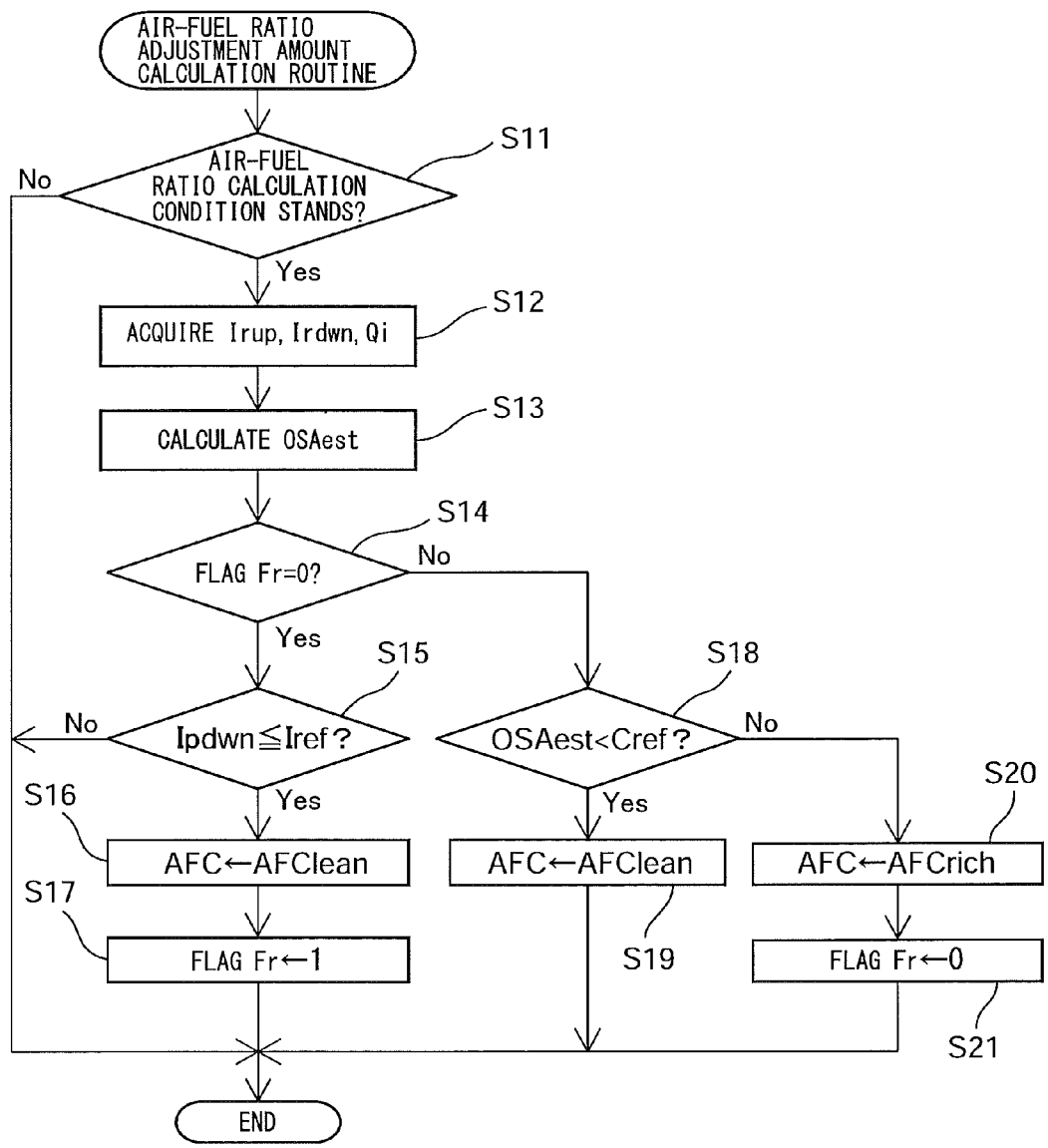
FIG. 13 is a flow chart which shows a control routine in control for calculating an air-fuel ratio adjustment amount.

Next, referring to FIGS. 12 and 13, a control system in the above embodiment will be specifically explained. The control system in the present embodiment, as shown by the functional block diagram of FIG. 12, is configured including the functional blocks A1 to A9. Below, each functional block will be explained while referring to FIG. 12.

<Calculation of Fuel Injection>

First, calculation of the fuel injection will be explained. In calculating the fuel injection, the cylinder intake air calculating means A1, basic fuel injection calculating means A2, and fuel injection calculating means A3 are used.

The cylinder intake air calculating means A1 calculates the intake air amount Mc to each cylinder based on the intake air flow rate Ga measured by the air flow meter 39, the engine speed NE calculated based on the output of the crank angle sensor 44, and the map or calculation formula stored in the ROM 34 of the ECU 31.

The basic fuel injection calculating means A2 divides the cylinder intake air amount Mc, which is calculated by the cylinder intake air calculating means A1, by the target air-fuel ratio AFT which is calculated by the later explained target air-fuel ratio setting means A6 to thereby calculate the basic fuel injection amount Qbase (Qbase=Mc/AFT).

The fuel injection calculating means A3 adds the basic fuel injection amount Qbase calculated by the basic fuel injection calculating means A2 and the later explained F/B correction amount DQi, to calculate the fuel injection amount Qi (Qi=Qbase+DQi). The fuel injector 11 is commanded to inject fuel so that the fuel of the fuel injection amount Qi which was calculated in this way is injected.

<Calculation of Target Air-Fuel Ratio>

Next, calculation of the target air-fuel ratio will be explained. In calculation of the target air-fuel ratio, an oxygen storage amount calculating means A4, target air-fuel ratio adjustment amount calculating means A5, and target air-fuel ratio setting means A6 are used.

The oxygen storage amount calculating means A4 calculates the estimated value OSAest of the oxygen storage amount of the upstream side exhaust purification catalyst 20, based on the fuel injection amount Qi calculated by the fuel injection calculating means A3 and the sensor output current Ipup of the upstream side air-fuel ratio sensor 40. For example, the oxygen storage amount calculating means A4 multiplies the difference between the air-fuel ratio corresponding to the sensor output current Ipup of the upstream side air-fuel ratio sensor 40 and the stoichiometric air-fuel ratio, with the fuel injection amount Qi, and cumulatively adds the calculated values to calculate the estimated value OSAest of the oxygen storage amount. Note that, the oxygen storage amount calculating means A4 need not constantly estimate the oxygen storage amount of the upstream side exhaust purification catalyst 20. For example, it is possible to estimate the oxygen storage amount only for the period from when the target air-fuel ratio is actually switched from the rich air-fuel ratio to the lean air-fuel ratio (time $t_3$ in FIG. 10) to when the estimated value OSAest of the oxygen storage amount reaches the judged reference storage amount Cref (time $t_4$ in FIG. 10).

In the target air-fuel ratio adjustment amount calculating means A5, the air-fuel ratio adjustment amount AFC of the target air-fuel ratio is calculated, based on the estimated value OSAest of the oxygen storage amount calculated by the oxygen storage amount calculating means A4 and the sensor output current Ipdwn of the downstream side air-fuel ratio sensor 41. Specifically, the air-fuel ratio adjustment amount AFC is set to the lean set adjustment amount AFClean when the sensor output current Ipdwn of the downstream side air-fuel ratio sensor 41 becomes the rich judgement reference value Iref (value corresponding to rich judged air-fuel ratio) or less. Then, the air-fuel ratio adjustment amount AFC is maintained at the lean set adjustment amount AFClean until the estimated value OSAest of the oxygen storage amount reaches the judged reference storage amount Cref. If the estimated value OSAest of the oxygen storage amount reaches the judged reference storage amount Cref, the air-fuel ratio adjustment amount AFC is set to the weak rich set adjustment amount AFCrich. After that, the air-fuel ratio adjustment amount AFC is maintained at a weak rich set adjustment amount AFCrich until the sensor output current Ipdwn of the downstream side air-fuel ratio sensor 41 becomes the rich judgement reference value Iref (value corresponding to the rich judged air-fuel ratio).

The target air-fuel ratio setting means A6 adds the reference air-fuel ratio, which is, in the present embodiment, the stoichiometric air-fuel ratio AFR, and the air-fuel ratio adjustment amount AFC calculated by the target air-fuel ratio adjustment amount calculating means A5 to thereby calculate the target air-fuel ratio AFT. Therefore, the target air-fuel ratio AFT is set to either a weak rich set air-fuel ratio which is slightly richer than the stoichiometric air-fuel ratio AFR (when the air-fuel ratio adjustment amount AFC is a weak rich set adjustment amount AFCrich) or a lean set air-fuel ratio which is leaner by a certain extent than the stoichiometric air-fuel ratio AFR (when the air-fuel ratio adjustment amount AFC is a lean set adjustment amount AFClean). The thus calculated target air-fuel ratio AFT is input to the basic fuel injection calculating means A2 and the later explained air-fuel ratio difference calculating means A8.

FIG. 13 is a flow chart which shows the control routine for control for calculation of the air-fuel ratio adjustment amount AFC. The illustrated control routine is performed by interruption every certain time interval.

As shown in FIG. 13, first, at step S11, it is judged if the calculating condition of the air-fuel ratio adjustment amount AFC stands. The calculating condition of the air-fuel ratio adjustment amount stands, for example, when a fuel cut control is not performed. If it is judged that the calculating condition of the air-fuel ratio stands at step S11, the routine proceeds to step S12. At step S12, the sensor output current Ipup of the upstream side air-fuel ratio sensor 40, the sensor output current Ipdwn of the downstream side air-fuel ratio sensor 41, and the fuel injection amount Qi are acquired. Next, at step S13, the estimated value OSAest of the oxygen storage amount is calculated, based on the sensor output current Ipup of the upstream side air-fuel ratio sensor 40 and the fuel injection amount Qi are which were acquired at step S12.

Next, at step S14, it is judged if the lean set flag Fr is set to 0. The lean set flag Fr is set to 1 if the air-fuel ratio adjustment amount AFC is set to the lean set adjustment amount AFClean, and is set to 0 otherwise. If the lean set flag Fr is set to 0 at step S14, the routine proceeds to step S15. At step S15, it is judged if the sensor output current Ipdwn of the downstream side air-fuel ratio sensor 41 is the rich judgement reference value Iref or less. When it is judged that the sensor output current Ipdwn of the downstream side air-fuel ratio sensor 41 is larger than the rich judgement reference value Iref, the control routine is ended.

On the other hand, if the oxygen storage amount OSAsc of the upstream side exhaust purification catalyst 20 decreases and the air-fuel ratio of the exhaust gas flowing out from the upstream side exhaust purification catalyst 20 falls, at step S15, it is judged that the sensor output current Ipdwn of the downstream side air-fuel ratio sensor 41 is the rich judgement reference value Iref or less. In this case, the routine proceeds to step S16 where the air-fuel ratio adjustment amount AFC is set to the lean set adjustment amount AFClean. Next, at step S17, the lean set flag Fr is set to 1 and the control routine is to ended.

In the next control routine, at step S14, it is judged that the lean set flag Fr is not set to 0 and the routine proceeds to step 18. At step S18, it is judged if the estimated value OSAest of the oxygen storage amount which was calculated at step S13 is smaller than the judged reference storage amount Cref. When it is judged that the estimated value OSAest of the oxygen storage amount is smaller than the judged reference storage amount Cref, the routine proceeds to step S19 where the air-fuel ratio adjustment amount AFC continues to be the lean set adjustment amount AFClean. On the other hand, if the oxygen storage amount of the upstream side exhaust purification catalyst 20 increases, finally it is judged at step S18 that the estimated value OSAest of the oxygen storage amount is the judged reference storage amount Cref or more and the routine proceeds to step S20. At step S20, the air-fuel ratio adjustment amount AFC is set to a weak rich set adjustment amount AFCrich, then, at step S21, the lean set flag Fr is reset to 0 and the control routine is ended.

<Calculation of F/B Correction Amount>

Returning again to FIG. 12, calculation of the F/B correction amount based on the sensor output current Ipup of the upstream side air-fuel ratio sensor 40 will be explained. In calculation of the F/B correction amount, the numerical value converting means A7, air-fuel ratio difference calculating means A8, and F/B correction amount calculating means A9 are used.

The numerical value converting means A7 calculates the upstream side exhaust air-fuel ratio AFup corresponding to the sensor output current Ipup based on the sensor output current Ipup of the upstream side air-fuel ratio sensor 40 and a map or calculation formula (for example, a map as shown in FIG. 5) which defines the relationship between the sensor output current Ipup and the air-fuel ratio of the air-fuel ratio sensor 40. Therefore, the upstream side exhaust air-fuel ratio AFup corresponds to the air-fuel ratio of the exhaust gas flowing into the upstream side exhaust purification catalyst 20.

The air-fuel ratio difference calculating means A8 subtracts the target air-fuel ratio AFT calculated by the target air-fuel ratio setting means A6 from the upstream side exhaust air-fuel ratio AFup calculated by the numerical value converting means A7 to thereby calculate the air-fuel ratio difference DAF (DAF=AFup−AFT). This air-fuel ratio difference DAF is a value which expresses excess/deficiency of the amount of fuel fed with respect to the target air-fuel ratio AFT.

The F/B correction amount calculating means A9 processes the air-fuel ratio difference DAF calculated by the air-fuel ratio difference calculating means A8 by proportional integral derivative processing (PID processing) to thereby calculate the F/B correction amount DFi for compensating for the excess/deficiency of the amount of feed of fuel based on the following equation (1). The thus calculated F/B correction amount DFi is input to the fuel injection calculating means A3.

$$DFi = Kp \cdot DAF + Ki \cdot SDAF + Kd \cdot DDAF \qquad (1)$$

Note that, in the above equation (1), $Kp$ is a preset proportional gain (proportional constant), $Ki$ is a preset integral gain (integral constant), and $Kd$ is a preset derivative gain (derivative constant). Further, DDAF is the time derivative value of the air-fuel ratio difference DAF and is calculated by dividing the difference between the currently updated air-fuel ratio difference DAF and the previously updated air-fuel ratio difference DAF by the time corresponding to the updating interval. Further, SDAF is the time derivative value of the air-fuel ratio difference DAF. This time derivative value DDAF is calculated by adding the previously updated time derivative value DDAF and the currently updated air-fuel ratio difference DAF (SDAF=DDAF+DAF).

Note that, in the above embodiment, the air-fuel ratio of the exhaust gas flowing into the upstream side exhaust purification catalyst 20 is detected by the upstream side air-fuel ratio sensor 40. However, the precision of detection of the air-fuel ratio of the exhaust gas flowing into the upstream side exhaust purification catalyst 20 does not necessarily have to be high, and therefore, for example, the air-fuel ratio of the exhaust gas may be estimated based on the fuel injection amount from the fuel injector 11 and output of the air flow meter 39.

Second Embodiment

Next, referring to FIG. 14 to FIG. 17, a control system of an internal combustion engine according to a second embodiment of the present invention will be explained. The configuration and control of the control system of an internal combustion engine according to the second embodiment are basically similar to the configuration and control of the control system of an internal combustion engine according to the above embodiment. However, in the above embodiment, at the upstream side air-fuel ratio sensor and the downstream side air-fuel ratio sensor, the same sensor applied voltages were applied, while in the present embodiment, different sensor applied voltages are applied between these air-fuel ratio sensors 75, 76.

<Micro Characteristics in Vicinity of Stoichiometric Air-Fuel Ratio of Reference Cell>

Figure 14:
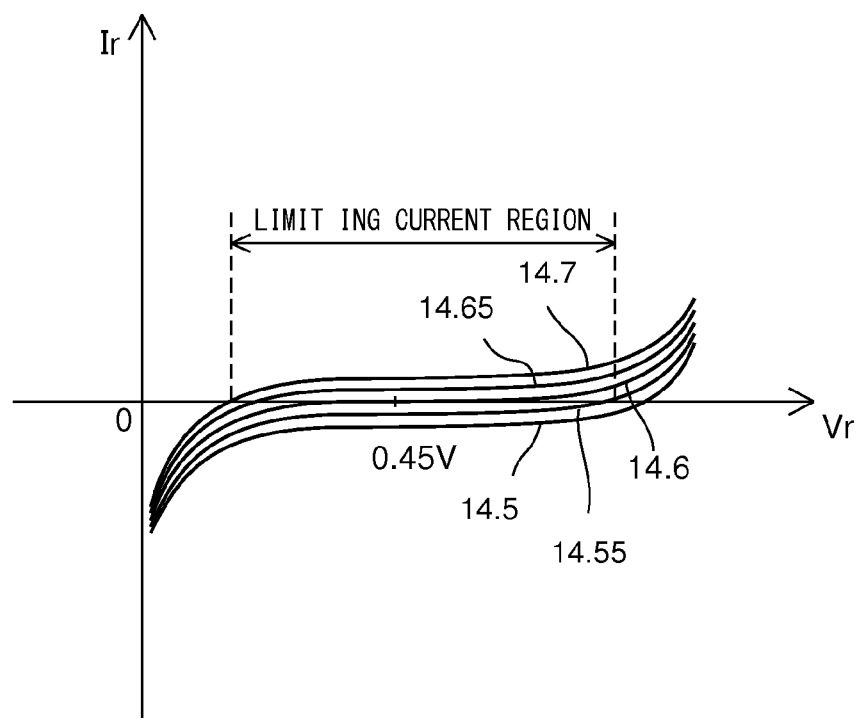
FIG. 14 is a view which shows a relationship between a sensor applied voltage and reference cell output current in a reference cell.

In this regard, if viewing the relationship between the sensor applied voltage Vr and reference cell output current Ir and the relationship between the exhaust air-fuel ratio and the reference cell output current Ir microscopically in the vicinity of the stoichiometric air-fuel ratio, the results become as shown in FIG. 14 and FIG. 15.

FIG. 14 is a view which shows the relationship between the sensor applied voltage Vr and reference cell output current Ir at the reference cell. As will be understood from FIG. 14, even at the limit current region (voltage region where reference cell output current does not change much at all even if changing applied voltage), when making the exhaust air-fuel ratio constant, along with an increase of the sensor applied voltage Vr, the reference cell output current Ir also increases, though the increase is very slight. Therefore, looking at the case where the exhaust air-fuel ratio is the stoichiometric air-fuel ratio (14.6) as an example, when the sensor applied voltage Vr is 0.45V or so, the reference cell output current Ir becomes 0. On the other hand, if the sensor applied voltage Vr is a certain degree lower than 0.45V (for example, 0.2V), the reference cell output current Ir becomes a value lower than 0. As opposed to this, if the sensor applied voltage Vr is a certain degree higher than 0.45V (for example, 0.7V), the reference cell output current Ir becomes higher than 0.

FIG. 15 is a view which shows the relationship between the exhaust air-fuel ratio and the reference cell output current Ir. From FIG. 15, it will be learned that at the region in the vicinity of the stoichiometric air-fuel ratio, the reference cell output current Ir for the same exhaust air-fuel ratio differs slightly for each sensor applied voltage Vr. For example, in the illustrated example, in the case where the exhaust air-fuel ratio is the stoichiometric air-fuel ratio, when the sensor applied voltage Vr is 0.45V, the reference cell output current Ir is 0. Further, if the sensor applied voltage Vr is larger than 0.45V, the reference cell output current Ir is also larger than 0, while if the sensor applied voltage Vr is smaller than 0.45V, the reference cell output current Ir is also smaller than 0.

In addition, from FIG. 15, it will be learned that at each sensor applied voltage Vr, the exhaust air-fuel ratio when the reference cell output current Ir becomes 0 (below, referred to as the "exhaust air-fuel ratio at the time of zero current") differs. In the illustrated example, in the case where the sensor applied voltage Vr is 0.45V, when the exhaust air-fuel ratio is the stoichiometric air-fuel ratio, the reference cell output current Ir becomes 0. As opposed to this, in the case where the sensor applied voltage Vr is larger than 0.45V, when the exhaust air-fuel ratio is richer than the stoichiometric air-fuel ratio, the reference cell output current Ir becomes 0, and the larger the sensor applied voltage Vr becomes, the smaller the exhaust air-fuel ratio at the time of zero current becomes. Conversely, in the case where the sensor applied voltage Vr is smaller than 0.45V, when the exhaust air-fuel ratio is leaner than the stoichiometric air-fuel ratio, the reference cell output current Ir becomes 0, and the smaller the sensor applied voltage Vr becomes, the larger the exhaust air-fuel ratio at the time of zero current becomes. That is, by making the sensor applied voltage Vr change, the exhaust air-fuel ratio at the time of zero current can be changed.

In this regard, the slope at FIG. 9, that is, the ratio of the increase amount of the reference cell output current to the increase amount of the exhaust air-fuel ratio (below, referred to as the "changing rate of the reference cell output current"), does not necessarily become the same even through similar production processes. Even with the same type of air-fuel ratio sensor, variations occur between specimens. In addition, even at the same air-fuel ratio sensor, the changing rate of output current changes due to aging, etc.

Figure 16:
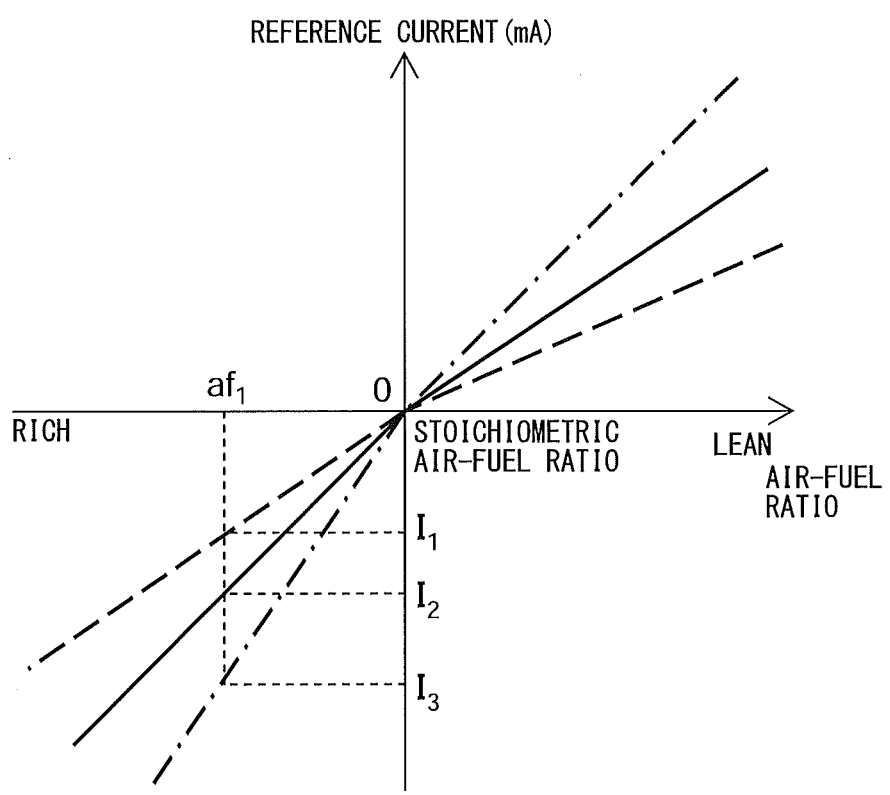
FIG. 16 is a view which shows a relationship between an exhaust air-fuel ratio and reference cell output current in a reference cell of an air-fuel ratio sensor.

This situation is shown in FIG. 16. FIG. 16 is a view which shows the relationship between the exhaust air-fuel ratio and reference cell output current at the reference cell of the air-fuel ratio sensor. For example, even when using the same model of reference cell which is configured to have output characteristics such as shown by the solid line A, depending on the sensor used or the usage time period, etc., the changing rate of the reference cell output current will become smaller as shown by the broken line B in FIG. 16, or the changing rate of the reference output current will become larger as shown by the one-dot chain line C.

Therefore, even when using the same model of air-fuel ratio sensor to measure the same air-fuel ratio of exhaust gas, the reference cell output current of the reference cell will become different, depending on the sensor used or the usage time period, etc. For example, when the reference cell has an output characteristic such as shown by the solid line A, the reference cell output current when measuring exhaust gas with an air-fuel ratio of $af_1$ becomes $I_2$. However, when the reference cell has an output characteristic such as shown by the broken line B or one-dot chain line C, the reference cell output currents when measuring exhaust gas with an air-fuel ratio of $af_1$, become respectively $I_1$ and $I_3$, and thus become reference cell output currents which differ from the above-mentioned $I_2$.

However, as will be understood from FIG. 16 as well, even if variations occur between specimens of air-fuel ratio sensors or variations occur in the same air-fuel ratio sensor due to aging, etc., the exhaust air-fuel ratio at the time of zero current (in example of FIG. 16, the stoichiometric air-fuel ratio) does not change much at all. That is, when the reference cell output current Ir becomes a value other than zero, the absolute value of the exhaust air-fuel ratio at that time will not necessarily be constant, but when the reference cell output current Ir is zero, the absolute value of the exhaust air-fuel ratio at that time (in the example of FIG. 16, the stoichiometric air-fuel ratio) will be constant.

Further, as explained using FIG. 15, in the air-fuel ratio sensors 75 and 76, the sensor applied voltage Vr can be changed so as to change the exhaust air-fuel ratio at the time of zero current. Further, if the reference cell output current which is detected by the reference cell output current detection device 71 is zero, the pump voltage which is applied by the pump voltage application device 72 will also be set to zero, and the pump current (sensor output current) Ip will also become zero. Therefore, according to the air-fuel ratio sensors 75 and 76, by changing the sensor applied voltage Vr, the absolute value of an exhaust air-fuel ratio other than the stoichiometric air-fuel ratio can be accurately detected.

In particular, when changing the sensor applied voltage Vr in the later explained "specific voltage region", the exhaust air-fuel ratio at the time of zero current can be adjusted only slightly from the stoichiometric air-fuel ratio (14.6) (for example, within a range of ±1% (about 14.45 to about 14.75)). Therefore, by suitably setting the sensor applied voltage Vr, it is possible to accurately detect the absolute value of an air-fuel ratio slightly different from the stoichiometric air-fuel ratio.

Note that, by changing the sensor applied voltage Vr as explained above, the exhaust air-fuel ratio at the time of zero current can be changed. However, if setting the sensor applied voltage Vr larger than a certain upper limit voltage or smaller than a certain lower limit voltage, the amount of change of the exhaust air-fuel ratio at the time of zero current with respect to the amount of change of the sensor applied voltage Vr becomes larger. Therefore, in such a voltage region, if the sensor applied voltage Vr deviates slightly, the exhaust air-fuel ratio at the time of zero current greatly changes. Therefore, in this voltage region, in order to accurately detect the absolute value of an exhaust air-fuel ratio, the sensor applied voltage Vr has to be precisely controlled, and this is not that practical. Therefore, from the viewpoint of accurately detecting the absolute value of the exhaust air-fuel ratio, the sensor applied voltage Vr has to be set to a value within a "specific voltage region" between a certain upper limit voltage and a certain lower limit voltage.

In this regard, as shown in FIG. 14, the air-fuel ratio sensors 75 and 76 have limit current regions of voltage regions where the reference cell output current Ir becomes the limit current for each exhaust air-fuel ratio. In the present embodiment, a limit current region when the exhaust air-fuel ratio is the stoichiometric air-fuel ratio is a "specific voltage region".

<Applied Voltage at Each Air-Fuel Ratio Sensor>

In the present embodiment, in consideration of the above-mentioned micro characteristics, when the air-fuel ratio of the exhaust gas is detected by the upstream side air-fuel ratio sensor 75, the sensor applied voltage Vrup at the upstream side air-fuel ratio sensor 75 is fixed to a voltage (for example, 0.45V) whereby the reference cell output becomes zero when the exhaust air-fuel ratio is the stoichiometric air-fuel ratio (in the present embodiment, 14.6). In other words, at the upstream side air-fuel ratio sensor 75, the sensor applied voltage Vrup is set so that the exhaust air-fuel ratio at the time of zero current becomes the stoichiometric air-fuel ratio.

On the other hand, when the air-fuel ratio of the exhaust gas is detected by the downstream side air-fuel ratio sensor 76, the sensor applied voltage Vr at the downstream side air-fuel ratio sensor 71 is fixed to a constant voltage (for example, 0.7V) by which the reference cell output current becomes zero when the exhaust air-fuel ratio is a predetermined rich judged air-fuel ratio (for example, 14.55) which is slightly richer than the stoichiometric air-fuel ratio. In other words, in the downstream side air-fuel ratio sensor 76, the sensor applied voltage Vrdwn is set so that the exhaust air-fuel ratio at the time of zero current becomes a rich judged air-fuel ratio which is slightly richer than the stoichiometric air-fuel ratio. In this way, in the present embodiment, the sensor applied voltage Vrdwn at the downstream side air-fuel ratio sensor 76 is set to a voltage which is higher than the sensor applied voltage Vrup at the upstream side air-fuel ratio sensor 75.

Therefore, the ECU 31 which is connected to the two air-fuel ratio sensors 75 and 76 judges that the exhaust air-fuel ratio around the upstream side air-fuel ratio sensor 75 is the stoichiometric air-fuel ratio when the sensor output current Ipup of the upstream side air-fuel ratio sensor 75 becomes zero. On the other hand, the ECU 31 judges that the exhaust air-fuel ratio around the downstream side air-fuel ratio sensor 76 is a rich judged air-fuel ratio, that is, a predetermined air-fuel ratio which differs from the stoichiometric air-fuel ratio, when the sensor output current Ipdwn of the downstream side air-fuel ratio sensor 76 becomes zero.

<Control of Air-Fuel Ratio in Second Embodiment>

The control of the air-fuel ratio in the second embodiment is basically similar to the control of the air-fuel ratio in the above embodiment. However, in the first embodiment, when, at the time $t_2$, the sensor output current Ipdwn of the downstream side air-fuel ratio sensor 41 has become the rich judged reference value Iref or less, the target air-fuel ratio is switched to the lean set air-fuel ratio. As opposed to this, in the present embodiment, when the sensor output current Ipdwn of the downstream side air-fuel ratio sensor 41 becomes zero or less, the target air-fuel ratio is switched to the lean set air-fuel ratio.

Figure 17:
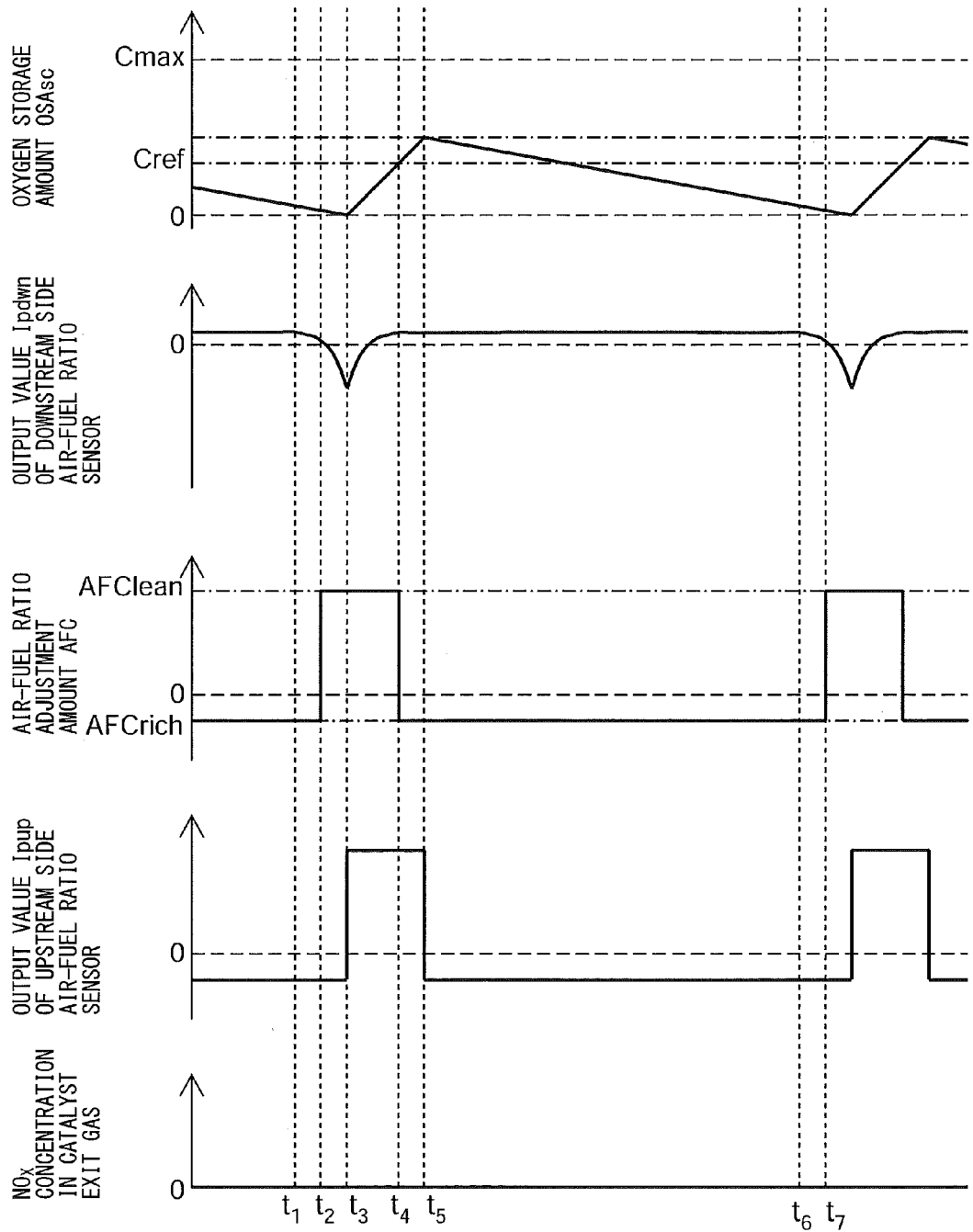
FIG. 17 is a view similar to FIG. 11, which shows a time chart of an oxygen storage amount OSAsc of an upstream side exhaust purification catalyst 20, etc.

FIG. 17 is a view similar to FIG. 11 and is a time chart of the oxygen storage amount OSAsc of the upstream side exhaust purification catalyst 20, etc., when performing the control in the present embodiment. Below, only the parts which differ from the control in FIG. 11 will be explained.

As will be understood from FIG. 17, before the time $t_1$, that is, when the air-fuel ratio of the exhaust gas flowing out from the upstream side exhaust purification catalyst 20 is the stoichiometric air-fuel ratio, the sensor output current Ipdwn of the downstream side air-fuel ratio sensor 76 becomes a value larger than zero. Then, part of the unburned gas in the exhaust gas flowing into the upstream side exhaust purification catalyst 20 from the time $t_1$ starts to flow out at the upstream side exhaust purification catalyst 20 without being purified. Along with this, the sensor output current Ipdwn of the downstream side air-fuel ratio sensor 76 becomes smaller toward zero, and becomes zero at the time $t_2$. In the present embodiment, if the sensor output current Ipdwn of the downstream side air-fuel ratio sensor 76 becomes zero or less, in order to suppress the decrease in the oxygen storage amount OSAsc of the upstream side exhaust purification catalyst 20, the air-fuel ratio adjustment amount AFC is switched to a value AFClean which corresponds to the lean set air-fuel ratio. The subsequent control is basically similar to the example which is shown in FIG. 11.

According to the present embodiment, as explained above, the absolute value at the rich judged air-fuel ratio can be detected by the downstream side air-fuel ratio sensor 41. As explained using FIG. 16, in a conventional air-fuel ratio sensor, it was difficult to accurately detect the absolute value of an air-fuel ratio other than the stoichiometric air-fuel ratio. Therefore, in a conventional air-fuel ratio sensor, if aging or individual differences, etc., cause error in the output current, even if the actual air-fuel ratio of the exhaust gas flowing out from the upstream side exhaust purification catalyst 20 differs from the rich judged air-fuel ratio, the output current of the air-fuel ratio sensor becomes a value which corresponds to the rich judged air-fuel ratio. As a result, the timing of switching the air-fuel ratio adjustment amount AFC from the slight rich set adjustment amount AFCrich to the lean set adjustment amount AFClean becomes delayed or this switching is performed at a timing at which switching is not required. As opposed to this, in the present embodiment, the absolute value at the rich judged air-fuel ratio can be accurately detected by the downstream side air-fuel ratio sensor 41. Therefore, delay in the timing of switching the air-fuel ratio adjustment amount AFC from the slight rich set adjustment amount AFCrich to the lean set adjustment amount AFClean, or switching at a timing not requiring switching, can be suppressed.

Third Embodiment

Next, referring to FIG. 18, a control system of an internal combustion engine according to a third embodiment of the present invention will be explained. The configuration of the control system of an internal combustion engine according to the third embodiment is basically similar to the configuration and control of the control system of an internal combustion engine according to the above embodiments. However, in the control system of the present embodiment, a diffusion regulating layer is provided around the gas chamber side electrode of the reference cell of the air-fuel ratio sensor.

Figure 18:
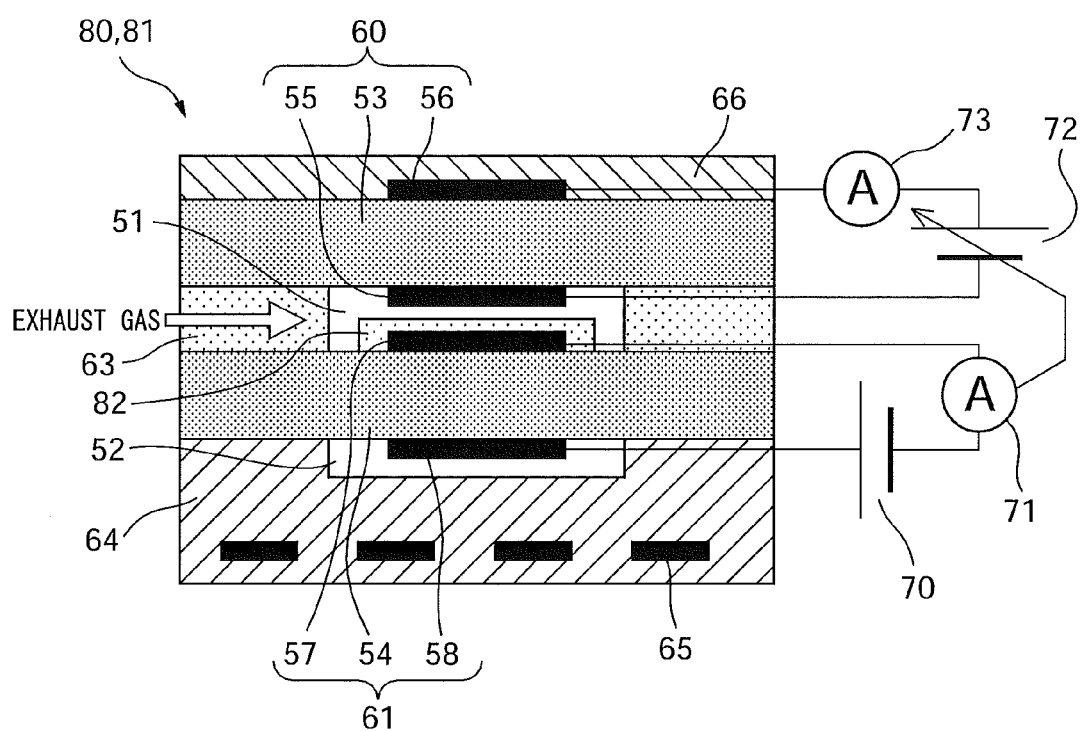
FIG. 18 is a cross-sectional view similar to FIG. 5, which schematically shows the configuration of an air-fuel ratio sensor of a third embodiment.

FIG. 18 schematically shows the configurations of the upstream side air-fuel ratio sensor 80 and the downstream side air-fuel ratio sensor 81 of the third embodiment, and is a cross-sectional view similar to FIG. 5. As will be understood from FIG. 18, each of the air-fuel ratio sensors 80, 81 has a reference cell diffusion regulating layer 82 which is provided at the inside of the measured gas chamber 51. The reference cell diffusion regulating layer 82 is arranged so as to surround the gas chamber side electrode 57 of the reference cell 61. Therefore, the gas chamber side electrode 57 is exposed through the reference cell diffusion regulating layer 82 to the measured gas chamber 51.

By providing a reference cell diffusion regulating layer 82 around the gas chamber side electrode 57 in this way, it is possible to regulate the diffusion of the exhaust gas flowing in around the gas chamber side electrode 57. In this regard, if not sufficiently regulating the diffusion of the exhaust gas flowing into the surroundings of the gas chamber side electrode 57, the relationship among the exhaust air-fuel ratio, sensor applied voltage Vr, and reference cell output current Ir will hardly have a trend such as shown in FIGS. 14 and 15. As a result, sometimes it is not possible to suitably detect the absolute value of an air-fuel ratio other than the stoichiometric air-fuel ratio. In the present embodiment, by sufficiently regulating the diffusion of the exhaust gas flowing into the surroundings of the gas chamber side electrode 57 by the reference cell diffusion regulating layer 82, it is possible to detect the absolute value of an air-fuel ratio which is different from the stoichiometric air-fuel ratio more reliably.

Note that, in this Description, the oxygen storage amount of the exhaust purification catalyst is explained as changing between the maximum oxygen storage amount and zero. This means that the amount of oxygen which can be further stored by the exhaust purification catalyst changes between zero (when oxygen storage amount is maximum oxygen storage amount) and the maximum value (when oxygen storage amount is zero).

REFERENCE SIGN LIST 5. combustion chamber
6. intake valve
8. exhaust valve
10. spark plug
11. fuel injector
13. intake branch pipe
15. intake pipe
18. throttle valve
19. exhaust manifold
20. upstream side exhaust purification catalyst
21. upstream side casing
22. exhaust pipe
23. downstream side casing
24. downstream side exhaust purification catalyst
31. ECU
39. air flow meter
40. upstream side air-fuel ratio sensor
41. downstream side air-fuel ratio sensor

The invention claimed is:
1. A control system of an internal combustion engine, comprising:
  an air-fuel ratio sensor which is provided in an exhaust passage of the internal combustion engine; and
  an engine control device which controls the internal combustion engine in accordance with a sensor output current of the air-fuel ratio sensor, wherein
    said air-fuel ratio sensor comprises:
      a measured gas chamber into which exhaust gas which is to be detected for air-fuel ratio flows;
      a pump cell which pumps in oxygen to and pumps out oxygen from the exhaust gas in the measured gas chamber in accordance with a pump current; and
      a reference cell with a detected reference cell output current which changes in accordance with the air-fuel ratio in said measured gas chamber,
    said reference cell comprises:
      a first electrode which is exposed to exhaust gas inside said measured gas chamber;
      a second electrode which is exposed to a reference atmosphere; and
      a solid electrolyte layer which is arranged between said first electrode and said second electrode, and
    said air-fuel ratio sensor further comprises:
      a reference cell voltage application device which applies a sensor applied voltage between the first electrode and second electrode of said reference cell;
      a reference cell output current detection device which detects a current which flows between the first electrode and second electrode of said reference cell as said reference cell output current;
      a pump current control device which controls a pump current, which flows at said pump cell, so that the reference cell output current which is detected by said reference cell output current detection device becomes a target current value; and
      a pump current detection device which detects the pump current as said sensor output current, wherein
        the target current value at said pump current control device is zero.

2. The control system of an internal combustion engine according to claim 1, wherein said air-fuel ratio sensor further comprises a diffusion regulating layer and the diffusion regulating layer is arranged so that a first electrode of said reference cell is exposed to exhaust gas inside the measured gas chamber through the diffusion regulating layer.

3. The control system of an internal combustion engine according to claim 1, wherein said air-fuel ratio sensor further comprises an atmospheric air chamber in which said second electrode is exposed, said reference atmosphere is the atmospheric air, and that atmospheric air chamber is configured so that atmospheric air can be introduced.

4. The control system of an internal combustion engine according to claim 1, wherein
  said pump cell comprises:
    a third electrode which is exposed to exhaust gas in said measured gas chamber;
    a fourth electrode which is exposed to exhaust gas around said air-fuel ratio sensor; and
    a solid electrolyte layer which is arranged between said third electrode and said fourth electrode, and
  said pump current control device controls the pump current which flows across said third electrode and fourth electrode through a solid electrolyte layer of said pump cell.

5. The control system of an internal combustion engine according to claim 1, wherein
  said reference cell is configured so that the sensor applied voltage, by which the reference cell output current becomes zero, changes in accordance with the air-fuel ratio of exhaust gas in the measured gas chamber and if increasing the sensor applied voltage at the reference cell when the exhaust gas is the stoichiometric air-fuel ratio, the reference cell output current increases along with that, and
  the sensor applied voltage at said reference cell is fixed to a constant voltage, and the constant voltage is a voltage by which the reference cell output current becomes zero when the air-fuel ratio of the exhaust gas in said measured gas chamber is the stoichiometric air-fuel ratio.

6. The control system of an internal combustion engine according to claim 5, wherein
  said internal combustion engine further comprises an exhaust purification catalyst which is provided at an upstream side, in the direction of flow of exhaust, from said air-fuel ratio sensor in said exhaust passage, and which can store oxygen, and said engine control device comprises:

an oxygen storage amount increasing means for making a target air-fuel ratio of exhaust gas which flows into said exhaust purification catalyst, continuously or intermittently leaner than the stoichiometric air-fuel ratio, when the sensor output current of said air-fuel ratio sensor has become a rich judged reference value corresponding to a rich judged air-fuel ratio lower than the stoichiometric air-fuel ratio, until the oxygen storage amount of said exhaust purification catalyst becomes a predetermined storage amount smaller than the maximum oxygen storage amount; and an oxygen storage amount decreasing means for making said target air-fuel ratio continuously or intermittently richer than the stoichiometric air-fuel ratio, when the oxygen storage amount of said exhaust purification catalyst has become said predetermined storage amount or more, so that the oxygen storage amount decreases toward zero without reaching the maximum oxygen storage amount.

7. The control system of an internal combustion engine according to claim 1, wherein said reference cell is configured so that the sensor applied voltage, by which the reference cell output current becomes zero, changes in accordance with the air-fuel ratio of exhaust gas in the measured gas chamber and if increasing the sensor applied voltage at the reference cell when the exhaust gas is the stoichiometric air-fuel ratio, the reference cell output current increases along with that, and the sensor applied voltage at said reference cell is fixed to a constant voltage, and the constant voltage is a voltage different from the voltage by which the reference cell output current becomes zero when the air-fuel ratio of the exhaust gas in said measured gas chamber is the stoichiometric air-fuel ratio and a voltage by which the reference cell output current becomes zero when the air-fuel ratio of said exhaust gas is an air-fuel ratio which is different from the stoichiometric air-fuel ratio.

8. The control system of an internal combustion engine according to claim 7, wherein said reference cell is configured so as to have a limit current region of a voltage region where said reference cell output current becomes a limit current for each exhaust air-fuel ratio, and said constant voltage is a voltage inside said limit current region when the exhaust air-fuel ratio is the stoichiometric air-fuel ratio.

9. The control system of an internal combustion engine according to claim 7, wherein said internal combustion engine comprises an exhaust purification catalyst which is provided at an upstream side, in the direction of flow of exhaust, from said air-fuel ratio sensor in said exhaust passage, and which can store oxygen, and said constant voltage is a voltage whereby said reference cell output current becomes zero when the exhaust air-fuel ratio is a predetermined air-fuel ratio which is richer than the stoichiometric air-fuel ratio.

10. The control system of an internal combustion engine according to claim 9, wherein said engine control device comprises:

an oxygen storage amount increasing means for making a target air-fuel ratio of exhaust gas which flows into said exhaust purification catalyst continuously or intermittently leaner than the stoichiometric air-fuel ratio, when the sensor output current of said air-fuel ratio sensor has become zero or less, until the oxygen storage amount of said exhaust purification catalyst becomes a predetermined storage amount smaller than the maximum oxygen storage amount; and an oxygen storage amount decreasing means for making said target air-fuel ratio continuously or intermittently richer than the stoichiometric air-fuel ratio, when the oxygen storage amount of said exhaust purification catalyst has become said predetermined storage amount or more, so that the oxygen storage amount decreases toward zero without reaching the maximum oxygen storage amount.

* * * * *

UNITED STATES PATENT AND TRADEMARK OFFICE
CERTIFICATE OF CORRECTION

PATENT NO. : 9,745,911 B2  
APPLICATION NO. : 14/763555  
DATED : August 29, 2017  
INVENTOR(S) : Go Hayashita et al.

Page 1 of 1

It is certified that error appears in the above-identified patent and that said Letters Patent is hereby corrected as shown below:

In the Specification

At Column 9, Line 48-50, change the content from:  
"$Bi_2O_2$, or other oxygen ion conducting oxide in which CaO, MgO, $Y_2O_2$, $Yb_2O_2$,"  
To:  
"$Bi_2O_3$, or other oxygen ion conducting oxide in which CaO, MgO, $Y_2O_3$, $Yb_2O_3$,"

Signed and Sealed this  
Twenty-second Day of May, 2018

Andrei Iancu  
*Director of the United States Patent and Trademark Office*